(12) United States Patent
Hastings et al.

(10) Patent No.: US 9,393,405 B2
(45) Date of Patent: Jul. 19, 2016

(54) WIRELESS TISSUE ELECTROSTIMULATION

(71) Applicant: Cardiac Pacemakers, Inc., St. Paul, MN (US)

(72) Inventors: Roger Hastings, Maple Grove, MN (US); John A. Becker, Delano, MN (US); Michael J. Pikus, Golden Valley, MN (US); Daniel M. Lafontaine, Plymouth, MN (US); Kevin D. Edmunds, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 149 days.

(21) Appl. No.: 14/264,663

(22) Filed: Apr. 29, 2014

(65) Prior Publication Data

US 2014/0236172 A1  Aug. 21, 2014

Related U.S. Application Data

(63) Continuation of application No. 12/361,884, filed on Jan. 29, 2009, now Pat. No. 8,738,147.

(60) Provisional application No. 61/059,993, filed on Jun. 9, 2008, provisional application No. 61/063,876, filed on Feb. 7, 2008.

(51) Int. Cl.
*A61N 1/05* (2006.01)
*A61N 1/372* (2006.01)
(Continued)

(52) U.S. Cl.
CPC .............. *A61N 1/057* (2013.01); *A61N 1/0565* (2013.01); *A61N 1/0573* (2013.01);
(Continued)

(58) Field of Classification Search
CPC .............. A61N 1/0565; A61N 1/0573; A61N 1/37223; A61N 1/3787; A61N 1/057; A61N 1/37205; A61N 1/3622; A61N 1/3624; A61N 1/037229; A61N 1/3756
See application file for complete search history.

(56) References Cited

U.S. PATENT DOCUMENTS 3,057,356 A 10/1962 Greatbatch
3,357,434 A 12/1967 Abel
(Continued)

FOREIGN PATENT DOCUMENTS

EP 0758542 A1 2/1997
EP 1166820 A2 1/2002
(Continued)

OTHER PUBLICATIONS

"U.S. Appl. No. 10/971,550, 312 Amendment filed Mar. 20, 09", 6 pgs.
(Continued)

*Primary Examiner* — Catherine Voorhees
(74) *Attorney, Agent, or Firm* — Seager, Tufte & Wickhem LLP

(57) ABSTRACT

A wireless electrostimulation system can comprise a wireless energy transmission source, and an implantable cardiovascular wireless electrostimulation node. A receiver circuit comprising an inductive antenna can be configured to capture magnetic energy to generate a tissue electrostimulation. A tissue electrostimulation circuit, coupled to the receiver circuit, can be configured to deliver energy captured by the receiver circuit as a tissue electrostimulation waveform. Delivery of tissue electrostimulation can be initiated by a therapy control unit.

17 Claims, 11 Drawing Sheets

(51) Int. Cl.
    *A61N 1/378*     (2006.01)
    *A61N 1/362*     (2006.01)
    *A61N 1/365*     (2006.01)
    *A61N 1/375*     (2006.01)

(52) U.S. Cl.
    CPC ......... *A61N 1/3787* (2013.01); *A61N 1/37223* (2013.01); *A61N 1/3622* (2013.01); *A61N 1/3624* (2013.01); *A61N 1/3756* (2013.01); *A61N 1/37205* (2013.01); *A61N 1/37229* (2013.01)

(56) References Cited

U.S. PATENT DOCUMENTS

| | | |
|---|---|---|
| 3,596,662 A | 8/1971 | Bolduc |
| 3,667,477 A | 6/1972 | Susset et al. |
| 3,713,449 A | 1/1973 | Mulier |
| 3,727,616 A | 4/1973 | Lenzkes |
| 3,835,864 A | 9/1974 | Rasor et al. |
| 3,902,501 A | 9/1975 | Citron et al. |
| 3,942,535 A | 3/1976 | Schulman |
| 3,943,936 A | 3/1976 | Rasor et al. |
| 4,010,756 A | 3/1977 | DuMont et al. |
| 4,157,720 A | 6/1979 | Greatbatch |
| 4,162,679 A | 7/1979 | Reenstierna |
| 4,198,991 A | 4/1980 | Harris |
| 4,256,115 A | 3/1981 | Bilitch |
| 4,441,210 A | 4/1984 | Hochmair et al. |
| 4,543,955 A | 10/1985 | Schroeppel |
| 4,641,664 A | 2/1987 | Botvidsson |
| 4,644,957 A | 2/1987 | Ricciardelli |
| 4,681,111 A | 7/1987 | Silvian |
| 4,721,118 A | 1/1988 | Harris |
| 4,830,006 A | 5/1989 | Haluska et al. |
| 4,858,623 A | 8/1989 | Bradshaw et al. |
| 4,860,750 A | 8/1989 | Frey et al. |
| 4,953,564 A | 9/1990 | Berthelsen |
| 4,987,897 A | 1/1991 | Funke |
| 5,012,806 A | 5/1991 | De Bellis |
| 5,113,869 A | 5/1992 | Nappholz et al. |
| 5,139,033 A | 8/1992 | Everett et al. |
| 5,143,090 A | 9/1992 | Dutcher et al. |
| 5,170,802 A | 12/1992 | Mehra |
| 5,178,149 A | 1/1993 | Imburgia et al. |
| 5,193,539 A | 3/1993 | Schulman et al. |
| 5,193,540 A | 3/1993 | Schulman et al. |
| 5,234,437 A | 8/1993 | Sepetka |
| 5,243,977 A | 9/1993 | Trabucco et al. |
| 5,246,014 A | 9/1993 | Williams et al. |
| 5,250,071 A | 10/1993 | Palermo |
| 5,255,693 A | 10/1993 | Dutcher et al. |
| 5,261,916 A | 11/1993 | Engelson |
| 5,300,107 A | 4/1994 | Stokes et al. |
| 5,304,195 A | 4/1994 | Twyford, Jr. et al. |
| 5,312,415 A | 5/1994 | Palermo |
| 5,312,439 A | 5/1994 | Loeb |
| 5,314,458 A | 5/1994 | Najafi et al. |
| 5,324,316 A | 6/1994 | Schulman et al. |
| 5,324,325 A | 6/1994 | Moaddeb |
| 5,335,664 A | 8/1994 | Nagashima |
| 5,336,252 A | 8/1994 | Cohen |
| 5,342,408 A | 8/1994 | deCoriolis et al. |
| 5,350,397 A | 9/1994 | Palermo et al. |
| 5,383,915 A | 1/1995 | Adams |
| 5,383,924 A | 1/1995 | Brehier |
| 5,405,367 A | 4/1995 | Schulman et al. |
| 5,411,535 A | 5/1995 | Fujii et al. |
| 5,411,537 A | 5/1995 | Munshi et al. |
| 5,447,533 A | 9/1995 | Vachon et al. |
| 5,487,760 A | 1/1996 | Villafana |
| 5,531,780 A | 7/1996 | Vachon |
| 5,571,148 A | 11/1996 | Loeb et al. |
| 5,591,217 A | 1/1997 | Barreras |
| 5,622,168 A | 4/1997 | Keusch et al. |
| 5,628,778 A | 5/1997 | Kruse et al. |
| 5,674,259 A | 10/1997 | Gray |
| 5,735,887 A | 4/1998 | Barreras, Sr. et al. |
| 5,755,764 A | 5/1998 | Schroeppel |
| 5,769,877 A | 6/1998 | Barreras, Sr. |
| 5,772,693 A | 6/1998 | Brownlee |
| 5,775,331 A | 7/1998 | Raymond et al. |
| 5,779,715 A | 7/1998 | Tu |
| 5,792,208 A | 8/1998 | Gray |
| 5,800,535 A | 9/1998 | Howard, III |
| 5,807,397 A | 9/1998 | Barreras |
| 5,814,089 A | 9/1998 | Stokes et al. |
| 5,833,715 A | 11/1998 | Vachon et al. |
| 5,851,227 A | 12/1998 | Spehr |
| 5,861,019 A | 1/1999 | Sun et al. |
| 5,871,532 A | 2/1999 | Schroeppel |
| 5,876,429 A | 3/1999 | Schroeppel |
| 5,876,431 A | 3/1999 | Spehr et al. |
| 5,954,757 A | 9/1999 | Gray |
| 5,995,876 A | 11/1999 | Kruse et al. |
| 6,006,139 A | 12/1999 | Kruse et al. |
| 6,035,239 A | 3/2000 | Patag et al. |
| 6,041,258 A | 3/2000 | Cigaina et al. |
| 6,044,300 A | 3/2000 | Gray |
| 6,123,724 A | 9/2000 | Denker |
| 6,132,456 A | 10/2000 | Sommer et al. |
| 6,141,588 A | 10/2000 | Cox et al. |
| 6,141,591 A | 10/2000 | Lenarz et al. |
| 6,144,879 A | 11/2000 | Gray |
| 6,144,880 A | 11/2000 | Ding et al. |
| 6,161,029 A | 12/2000 | Spreigl et al. |
| 6,164,284 A | 12/2000 | Schulman et al. |
| 6,200,303 B1 | 3/2001 | Verrior et al. |
| 6,208,894 B1 | 3/2001 | Schulman et al. |
| 6,223,079 B1 | 4/2001 | Bakels et al. |
| 6,240,316 B1 | 5/2001 | Richmond et al. |
| 6,266,567 B1 | 7/2001 | Ishikawa et al. |
| 6,315,721 B2 | 11/2001 | Schulman et al. |
| 6,336,937 B1 | 1/2002 | Vonesh et al. |
| 6,345,202 B2 | 2/2002 | Richmond et al. |
| 6,351,673 B1 | 2/2002 | Ding et al. |
| 6,360,127 B1 | 3/2002 | Ding et al. |
| 6,363,279 B1 | 3/2002 | Ben-Haim et al. |
| 6,363,938 B2 | 4/2002 | Saadat et al. |
| 6,370,434 B1 | 4/2002 | Zhang et al. |
| 6,381,495 B1 | 4/2002 | Jenkins |
| 6,385,472 B1 | 5/2002 | Hall et al. |
| 6,409,674 B1 | 6/2002 | Brockway et al. |
| 6,441,747 B1 | 8/2002 | Khair et al. |
| 6,445,953 B1 | 9/2002 | Bulkes et al. |
| 6,456,256 B1 | 9/2002 | Amundson et al. |
| 6,501,983 B1 | 12/2002 | Natarajan et al. |
| 6,510,345 B1 | 1/2003 | Van Bentem |
| 6,542,775 B2 | 4/2003 | Ding et al. |
| 6,556,874 B2 | 4/2003 | Audoglio |
| 6,564,807 B1 | 5/2003 | Schulman et al. |
| 6,574,510 B2 | 6/2003 | Von Arx et al. |
| 6,582,441 B1 | 6/2003 | He et al. |
| 6,589,230 B2 | 7/2003 | Gia et al. |
| 6,614,406 B2 | 9/2003 | Amundson et al. |
| 6,647,292 B1 | 11/2003 | Bardy et al. |
| 6,783,499 B2 | 8/2004 | Schwartz |
| 6,856,836 B2 | 2/2005 | Ding et al. |
| 6,859,665 B2 | 2/2005 | Ding et al. |
| 6,895,265 B2 | 5/2005 | Silver |
| 6,895,280 B2 | 5/2005 | Meadows et al. |
| 6,897,788 B2 | 5/2005 | Khair et al. |
| 6,907,285 B2 | 6/2005 | Denker et al. |
| 6,917,833 B2 | 7/2005 | Denker et al. |
| 6,978,173 B2 | 12/2005 | Stoll et al. |
| 7,003,350 B2 | 2/2006 | Denker et al. |
| 7,006,864 B2 | 2/2006 | Echt et al. |
| 7,050,849 B2 | 5/2006 | Echt et al. |
| 7,054,691 B1 | 5/2006 | Kuzma et al. |
| 7,062,318 B2 | 6/2006 | Ben-Haim et al. |
| 7,076,305 B2 | 7/2006 | Imran et al. |
| 7,184,830 B2 | 2/2007 | Echt et al. |
| 7,200,437 B1 | 4/2007 | Nabutovsky et al. |
| 7,209,783 B2 | 4/2007 | Fellows et al. |

(56) References Cited

U.S. PATENT DOCUMENTS

| | | |
|---|---|---|
| 7,231,260 B2 | 6/2007 | Wallace et al. |
| 7,289,853 B1 | 10/2007 | Campbell et al. |
| 7,410,497 B2 | 8/2008 | Hastings et al. |
| 7,522,962 B1 | 4/2009 | Doron et al. |
| 7,532,932 B2 | 5/2009 | Denker et al. |
| 7,532,933 B2 | 5/2009 | Hastings et al. |
| 7,558,631 B2 | 7/2009 | Cowan et al. |
| 7,565,195 B1 | 7/2009 | Kroll et al. |
| 7,606,621 B2 | 10/2009 | Brisken et al. |
| 7,610,092 B2 | 10/2009 | Cowan et al. |
| 7,615,010 B1 | 11/2009 | Najafi et al. |
| 7,634,313 B1 | 12/2009 | Kroll et al. |
| 7,647,109 B2 | 1/2010 | Hastings et al. |
| 7,650,186 B2 | 1/2010 | Hastings et al. |
| 7,702,392 B2 | 4/2010 | Echt et al. |
| 7,765,001 B2 | 7/2010 | Echt et al. |
| 7,809,438 B2 | 10/2010 | Echt et al. |
| 7,840,281 B2 | 11/2010 | Kveen et al. |
| 7,848,815 B2 | 12/2010 | Brisken et al. |
| 7,848,823 B2 | 12/2010 | Drasler et al. |
| 7,877,136 B1 | 1/2011 | Moffitt et al. |
| 7,877,142 B2 | 1/2011 | Moaddeb et al. |
| 7,890,173 B2 | 2/2011 | Brisken et al. |
| 7,894,904 B2 | 2/2011 | Cowan et al. |
| 7,894,907 B2 | 2/2011 | Cowan et al. |
| 7,894,910 B2 | 2/2011 | Cowan et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,904,170 B2 | 3/2011 | Harding |
| 7,937,148 B2 | 5/2011 | Jacobson |
| 7,937,161 B2 | 5/2011 | Hastings et al. |
| 7,945,333 B2 | 5/2011 | Jacobson |
| 7,996,087 B2 | 8/2011 | Cowan et al. |
| 8,010,209 B2 | 8/2011 | Jacobson |
| 8,019,419 B1 | 9/2011 | Panescu et al. |
| 8,032,219 B2 | 10/2011 | Neumann et al. |
| 8,050,774 B2 | 11/2011 | Kveen et al. |
| 8,165,694 B2 | 4/2012 | Carbanaru et al. |
| 8,185,213 B2 | 5/2012 | Kveen et al. |
| 8,204,595 B2 | 6/2012 | Pianca et al. |
| 8,204,605 B2 | 6/2012 | Hastings et al. |
| 8,260,416 B2 | 9/2012 | Ben-Haim et al. |
| 8,290,600 B2 | 10/2012 | Hastings et al. |
| 8,332,036 B2 | 12/2012 | Hastings et al. |
| 8,340,780 B2 | 12/2012 | Hastings et al. |
| 8,478,408 B2 | 7/2013 | Hastings et al. |
| 2001/0018547 A1 | 8/2001 | Mechlenburg et al. |
| 2002/0026228 A1 | 2/2002 | Schauerte |
| 2002/0052632 A1 | 5/2002 | Ben-Haim et al. |
| 2002/0065543 A1 | 5/2002 | Gomperz et al. |
| 2002/0077556 A1 | 6/2002 | Schwartz |
| 2002/0123774 A1 | 9/2002 | Loeb et al. |
| 2002/0123785 A1 | 9/2002 | Zhang et al. |
| 2002/0138009 A1 | 9/2002 | Brockway et al. |
| 2002/0183791 A1 | 12/2002 | Denker et al. |
| 2002/0198604 A1 | 12/2002 | Schulman et al. |
| 2003/0036773 A1 | 2/2003 | Whitehurst et al. |
| 2003/0050681 A1 | 3/2003 | Pianca et al. |
| 2003/0074041 A1 | 4/2003 | Parry et al. |
| 2003/0088278 A1 | 5/2003 | Bardy |
| 2003/0109914 A1 | 6/2003 | Westlund et al. |
| 2003/0158584 A1 | 8/2003 | Cates et al. |
| 2003/0181958 A1 | 9/2003 | Dobak |
| 2003/0181959 A1 | 9/2003 | Dobak |
| 2004/0059392 A1 | 3/2004 | Parramon et al. |
| 2004/0087831 A1 | 5/2004 | Michels et al. |
| 2004/0098068 A1 | 5/2004 | Carbunaru et al. |
| 2004/0102830 A1 | 5/2004 | Williams |
| 2004/0103906 A1 | 6/2004 | Schulman et al. |
| 2004/0106954 A1 | 6/2004 | Whitehurst et al. |
| 2004/0147973 A1 | 7/2004 | Hauser et al. |
| 2004/0171355 A1 | 9/2004 | Yu et al. |
| 2004/0172083 A1 | 9/2004 | Penner |
| 2004/0176822 A1 | 9/2004 | Thompson et al. |
| 2004/0215280 A1 | 10/2004 | Dublin et al. |
| 2005/0021108 A1 | 1/2005 | Klosterman et al. |
| 2005/0025797 A1 | 2/2005 | Wang et al. |
| 2005/0043765 A1 | 2/2005 | Williams et al. |
| 2005/0057905 A1 | 3/2005 | He et al. |
| 2005/0060011 A1 | 3/2005 | Denker et al. |
| 2005/0096702 A1 | 5/2005 | Denker et al. |
| 2005/0131511 A1 | 6/2005 | Westlund |
| 2005/0149138 A1 | 7/2005 | Min et al. |
| 2005/0182456 A1 | 8/2005 | Ziobro et al. |
| 2005/0182465 A1 | 8/2005 | Ness |
| 2005/0251238 A1 | 11/2005 | Wallace et al. |
| 2005/0251240 A1 | 11/2005 | Doan |
| 2005/0261741 A1 | 11/2005 | Libbus et al. |
| 2005/0288596 A1 | 12/2005 | Eigler |
| 2005/0288727 A1 | 12/2005 | Penner |
| 2006/0015097 A1 | 1/2006 | Mulier et al. |
| 2006/0020316 A1 | 1/2006 | Martinez et al. |
| 2006/0064135 A1 | 3/2006 | Brockway |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095089 A1 | 5/2006 | Soykan et al. |
| 2006/0136001 A1 | 6/2006 | Ortega et al. |
| 2006/0136004 A1 | 6/2006 | Cowan et al. |
| 2006/0173504 A1 | 8/2006 | Zhu et al. |
| 2006/0173505 A1 | 8/2006 | Salo et al. |
| 2006/0178719 A1 | 8/2006 | Ideker et al. |
| 2006/0206170 A1 | 9/2006 | Denker et al. |
| 2006/0241705 A1 | 10/2006 | Neumann et al. |
| 2007/0075905 A1 | 4/2007 | Denker et al. |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088418 A1 | 4/2007 | Jacobson |
| 2007/0106357 A1 | 5/2007 | Denker et al. |
| 2007/0135882 A1 | 6/2007 | Drasler et al. |
| 2007/0135883 A1 | 6/2007 | Drasler et al. |
| 2007/0150009 A1 | 6/2007 | Kveen et al. |
| 2007/0150037 A1 | 6/2007 | Hastings et al. |
| 2007/0150038 A1 | 6/2007 | Hastings et al. |
| 2007/0162079 A1 | 7/2007 | Shemer et al. |
| 2007/0203556 A1 | 8/2007 | Rutten et al. |
| 2007/0219590 A1 | 9/2007 | Hastings et al. |
| 2007/0239248 A1* | 10/2007 | Hastings ............ A61N 1/0573 607/127 |
| 2007/0276444 A1 | 11/2007 | Gelbart et al. |
| 2007/0293904 A1 | 12/2007 | Gelbart et al. |
| 2008/0021505 A1 | 1/2008 | Hastings et al. |
| 2008/0021532 A1* | 1/2008 | Kveen .................. A61N 1/362 607/115 |
| 2008/0039904 A1 | 2/2008 | Bulkes et al. |
| 2008/0046040 A1 | 2/2008 | Denker et al. |
| 2008/0077184 A1 | 3/2008 | Denker et al. |
| 2008/0077188 A1 | 3/2008 | Denker et al. |
| 2008/0109054 A1 | 5/2008 | Hastings et al. |
| 2008/0119911 A1 | 5/2008 | Rosero |
| 2008/0140142 A1 | 6/2008 | Darvish et al. |
| 2008/0262588 A1 | 10/2008 | Zarembo et al. |
| 2008/0288039 A1 | 11/2008 | Reddy |
| 2008/0306359 A1 | 12/2008 | Zdeblick et al. |
| 2008/0319502 A1 | 12/2008 | Sunagawa et al. |
| 2009/0018599 A1 | 1/2009 | Hastings et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0204170 A1 | 8/2009 | Hastings et al. |
| 2009/0234407 A1 | 9/2009 | Hastings et al. |
| 2009/0275998 A1 | 11/2009 | Burnes et al. |
| 2010/0094367 A1 | 4/2010 | Sen |
| 2010/0100144 A1 | 4/2010 | Shuros et al. |
| 2010/0198288 A1 | 8/2010 | Ostroff |
| 2010/0228308 A1 | 9/2010 | Cowan et al. |
| 2010/0286744 A1 | 11/2010 | Echt et al. |
| 2010/0314775 A1 | 12/2010 | Schwarzbauer |
| 2011/0034939 A1 | 2/2011 | Kveen et al. |
| 2011/0071586 A1 | 3/2011 | Jacobson |

(56) References Cited

U.S. PATENT DOCUMENTS

| | | |
|---|---|---|
| 2011/0077708 A1 | 3/2011 | Ostroff |
| 2011/0190835 A1 | 8/2011 | Brockway et al. |
| 2011/0208260 A1 | 8/2011 | Jacobson |
| 2011/0213233 A1 | 9/2011 | Stevenson et al. |
| 2011/0218587 A1 | 9/2011 | Jacobson |
| 2011/0237967 A1 | 9/2011 | Moore et al. |
| 2011/0251660 A1 | 10/2011 | Griswold |
| 2011/0251662 A1 | 10/2011 | Griswold et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2012/0078322 A1 | 3/2012 | Dal Molin et al. |
| 2012/0089198 A1 | 4/2012 | Ostroff |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0158111 A1 | 6/2012 | Khairkhahan et al. |
| 2012/0172690 A1 | 7/2012 | Anderson et al. |
| 2012/0232565 A1 | 9/2012 | Kveen et al. |
| 2013/0268042 A1 | 10/2013 | Hastings et al. |

FOREIGN PATENT DOCUMENTS

| | | |
|---|---|---|
| EP | 1166832 A1 | 1/2002 |
| EP | 1809372 A1 | 7/2007 |
| EP | 1812104 A1 | 8/2007 |
| EP | 1835962 A1 | 9/2007 |
| EP | 2254663 B1 | 8/2012 |
| EP | 2001552 B1 | 9/2012 |
| FR | 2559391 | 8/1985 |
| JP | 61203730 A | 9/1986 |
| JP | 62-254770 A | 6/1987 |
| JP | 02307481 A | 12/1990 |
| JP | 05-245215 A | 9/1993 |
| JP | 5245215 | 9/1993 |
| JP | 2005245215 A | 9/1993 |
| JP | 6510459 A | 11/1994 |
| JP | 7016299 A | 1/1995 |
| JP | 9508054 A | 8/1997 |
| JP | 10-509901 | 9/1998 |
| JP | 2000-502931 A | 3/2000 |
| JP | 2001511406 A | 8/2001 |
| JP | 2002510222 A | 4/2002 |
| JP | 2002-514478 A | 5/2002 |
| JP | 2004-173790 A | 6/2004 |
| JP | 2010509901 | 3/2010 |
| JP | 5153892 B2 | 2/2013 |
| NO | WO-9725098 A1 | 7/1997 |
| NO | WO-9906102 A1 | 2/1999 |
| NZ | 526115 | 10/2006 |
| NZ | 539770 | 10/2007 |
| NZ | 539771 | 10/2007 |
| WO | WO-9308871 A1 | 5/1993 |
| WO | WO-9510226 A1 | 4/1995 |
| WO | WO-9620754 A1 | 7/1996 |
| WO | WO-9826840 A1 | 6/1998 |
| WO | WO-9906102 A1 | 2/1999 |
| WO | WO-9958191 A1 | 11/1999 |
| WO | WO-9964104 A1 | 12/1999 |
| WO | WO-0030534 A1 | 6/2000 |
| WO | WO-0100114 A1 | 1/2001 |
| WO | WO03076010 | 9/2003 |
| WO | WO-2004002572 A1 | 1/2004 |
| WO | WO-2004012811 A1 | 2/2004 |
| WO | WO-2005101660 A1 | 10/2005 |
| WO | WO-2006045073 A1 | 4/2006 |
| WO | WO-2006045074 A2 | 4/2006 |
| WO | WO-2006045075 A1 | 4/2006 |
| WO | WO-2006096685 A1 | 9/2006 |
| WO | WO-2007067231 A1 | 6/2007 |
| WO | WO-2007067253 A1 | 6/2007 |
| WO | WO-2007078770 A2 | 7/2007 |
| WO | WO-2007112004 A2 | 10/2007 |
| WO | WO-2007115044 A2 | 10/2007 |
| WO | WO-2008011626 A1 | 1/2008 |
| WO | WO-2008034005 A2 | 3/2008 |
| WO | WO-2008111998 A1 | 9/2008 |
| WO | WO-2009099550 A1 | 8/2009 |
| WO | WO-2009099597 A1 | 8/2009 |
| WO | WO-2012082755 A1 | 6/2012 |

OTHER PUBLICATIONS

"U.S. Appl. No. 10/971,550, Examiner Interview Summary mailed Jan. 22, 2008", 4 pgs.

"U.S. Appl. No. 10/971,550, Non Final Office Action mailed Mar. 19, 2007", 11 pgs.

"U.S. Appl. No. 10/971,550, Non-Final Office Action mailed Nov. 5, 2007", 19 pgs.

"U.S. Appl. No. 10/971,550, Notice of Allowance mailed Jul. 14, 2008", 4 pgs.

"U.S. Appl. No. 10/971,550, Notice of Allowance mailed Dec. 22, 2008", 4 pgs.

"U.S. Appl. No. 10/971,550, PTO Response to 312 Amendment mailed Apr. 6, 2009", 2 pgs.

"U.S. Appl. No. 10/971,550, Response filed Mar. 25, 2008 to Non Final Office Action mailed Nov. 5, 2007", 17 pgs.

"U.S. Appl. No. 10/971,550, Response filed Sep. 4, 2007 to Non-Final Office Action mailed Mar. 19, 2007", 15 pgs.

"U.S. Appl. No. 11/075,375, Examiner Interview Summary mailed Jan. 12, 2009", 4 pgs.

"U.S. Appl. No. 11/075,375, Examiner Interview Summary mailed May 1, 2008", 4 pgs.

"U.S. Appl. No. 11/075,375, Final Office Action mailed Jan. 23, 2008", 10 pgs.

"U.S. Appl. No. 11/075,375, Final Office Action mailed Apr. 16, 2009", 10 pgs.

"U.S. Appl. No. 11/075,375, Non-Final Office Action mailed Jun. 8, 2007", 11 pgs.

"U.S. Appl. No. 11/075,375, Non-Final Office Action mailed Aug. 11, 2008", 15 pgs.

"U.S. Appl. No. 11/075,375, Notice of Allowance mailed Sep. 4, 2009", 6 pgs.

"U.S. Appl. No. 11/075,375, Response filed Jan. 12, 2009 to Non-Final Office Action mailed Aug. 11, 2008", 18 pgs.

"U.S. Appl. No. 11/075,375, Response filed May 22, 2008 to Final Office Action mailed Jan. 23, 2008", 16 pgs.

"U.S. Appl. No. 11/075,375, Response filed Jul. 16, 2009 to Final Office Action mailed Apr. 16, 2009", 13 pgs.

"U.S. Appl. No. 11/075,375, Response filed Oct. 26, 2007 to Non-Final Office Action mailed Jun. 8, 2007", 10 pgs.

"U.S. Appl. No. 11/075,376, Final Office Action mailed Jan. 7, 2008", 11 pgs.

"U.S. Appl. No. 11/075,376, Non-Final Office Action mailed Jun. 26, 2007", 9 pgs.

"U.S. Appl. No. 11/075,376, Non-Final Office Action mailed Aug. 20, 2008", 16 pgs.

"U.S. Appl. No. 11/075,376, Examiner Interview Summary mailed Jan. 12, 2009", 4 pgs.

"U.S. Appl. No. 11/075,376, Examiner interview Summary mailed Apr. 2, 2008", 4 pgs.

"U.S. Appl. No. 11/075,376, Final Office Action mailed Apr. 8, 2009", 17 pgs.

"U.S. Appl. No. 11/075,376, Notice of Allowance mailed Aug. 24, 2009", 6 pgs.

"U.S. Appl. No. 11/075,376, Response filed Jan. 21, 2009 to Non-Final Office Action mailed Aug. 20, 2008", 22 pgs.

"U.S. Appl. No. 11/075,376, Response filed Jun. 9, 2008 to Final Office Action mailed Jan. 7, 2008", 20 pgs.

"U.S. Appl. No. 11/075,376, Response filed Jul. 8, 2009 to Final Office Action mailed Apr. 8, 2009", 11 pgs.

"U.S. Appl. No. 11/075,376, Response filed Oct. 26, 2007 to Non-Final Office Action mailed Jun. 26, 2007", 14 pgs.

"U.S. Appl. No. 11/316,120, Final Office Action mailed Aug. 20, 2008", 9 pgs.

(56) References Cited

OTHER PUBLICATIONS

"U.S. Appl. No. 11/316,120, Non-Final Office Action mailed Apr. 17, 2009", 8 pgs.
"U.S. Appl. No. 11/316,120, Decision on Pre-Appeal Brief Request mailed Apr. 19, 2011", 2 pgs.
"U.S. Appl. No. 11/316,120, Final Office Action mailed Oct. 28, 2010", 8 pgs.
"U.S. Appl. No. 11/316,120, Final Office Action mailed Nov. 12, 2009", 8 pgs.
"U.S. Appl. No. 11/316,120, Non Final Office Action mailed Apr. 11, 2008", 7 pgs.
"U.S. Appl. No. 11/316,120, Non-Final Office Action mailed May 27, 2010", 7 pgs.
"U.S. Appl. No. 11/316,120, Notice of Allowance mailed Jul. 20, 2011", 7 pgs.
"U.S. Appl. No. 11/316,120, Pre-Appeal Brief Request filed Mar. 25, 2011", 5 pgs.
"U.S. Appl. No. 11/316,120, Response filed Mar. 25, 2011 to Final Office Action mailed Oct. 28, 2010", 8 pgs.
"U.S. Appl. No. 11/316,120, Response filed Apr. 12, 2010 to Final Office Action mailed Nov. 12, 2009", 12 pgs.
"U.S. Appl. No. 11/316,120, Response filed May 14, 2008 to Non Final Office Action mailed Apr. 11, 2008", 12 pgs.
"U.S. Appl. No. 11/316,120, Response filed Jul. 17, 2009 to Non Final Office Action mailed Apr. 17, 2009", 13 pgs.
"U.S. Appl. No. 11/316,120, Response filed Aug. 27, 2010 to Non Final Office Action mailed May 27, 2010", 13 pgs.
"U.S. Appl. No. 11/316,120, Response filed Dec. 22, 2008 to Final Office Action mailed Aug. 20, 2008", 13 pgs.
"U.S. Appl. No. 11/316,120, Supplemental Notice of Allowance mailed Sep. 1, 2011", 4 pgs.
"U.S. Appl. No. 11/394,601, Decision on Pre-Appeal Brief Request mailed Oct. 6, 2010", 2 pgs.
"U.S. Appl. No. 11/394,601, Final Office Action mailed Mar. 22, 2010", 7 pgs.
"U.S. Appl. No. 11/394,601, Non-Final Office Action mailed Sep. 2, 2009", 6 pgs.
"U.S. Appl. No. 11/394,601, Notice of Allowance mailed Dec. 28, 2010", 8 pgs.
"U.S. Appl. No. 11/394,601, Pre-Appeal Brief Request filed Jul. 21, 2010", 5 pgs.
"U.S. Appl. No. 11/394,601, Response filed May 4, 2009 to Restriction Requirement mailed Apr. 2, 2009", 9 pgs.
"U.S. Appl. No. 11/394,601, Response filed Dec. 2, 2009 to Non Final Office Action mailed Sep. 2, 2009", 11 pgs.
"U.S. Appl. No. 11/394,601, Restriction Requirement mailed Apr. 2, 2009", 10 pgs.
"U.S. Appl. No. 11/490,576, Decision on Pre-Appeal Brief Request mailed Aug. 30, 2011", 2 pgs.
"U.S. Appl. No. 11/490,576, Final Office Action mailed Jan. 19, 2011", 12 pgs.
"U.S. Appl. No. 11/490,576, Non Final Office Action mailed Jul. 9, 2008", 16 pgs.
"U.S. Appl. No. 11/490,576, Non Final Office Action mailed Nov. 9, 2011", 8 pgs.
"U.S. Appl. No. 11/490,576, Non-Final Office Action mailed Feb. 17, 2009", 8 pgs.
"U.S. Appl. No. 11/490,576, Non-Final Office Action mailed Jul. 12, 2010", 8 pgs.
"U.S. Appl. No. 11/490,576, Non-Final Office Action mailed Oct. 5, 2009", 8 pgs.
"U.S. Appl. No. 11/490,576, Notice of Allowance mailed Jun. 4, 2012", 8 pgs.
"U.S. Appl. No. 11/490,576, Pre-Appeal Brief Request filed May 12, 2011", 5 pgs.
"U.S. Appl. No. 11/490,576, Response filed Mar. 5, 2010 to Non Final Office Action mailed Oct. 5, 2009", 13 pgs.
"U.S. Appl. No. 11/490,576, Response filed Apr. 9, 2012 to Non Final Office Action mailed Nov. 9, 2011", 11 pgs.
"U.S. Appl. No. 11/490,576, Response filed Jun. 17, 2009 to Non Final Office Action mailed Feb. 17, 2009", 13 pgs.
"U.S. Appl. No. 11/490,576, Response filed Oct. 4, 2010 to Non Final Office Action mailed Jul. 12, 2010", 15 pgs.
"U.S. Appl. No. 11/490,576, Response filed Nov. 10, 2008 to Non-Final Office Action mailed Jul. 9, 2008", 20 pgs.
"U.S. Appl. No. 11/490,916, Examiner Interview Summary mailed Apr. 12, 2010", 3 pgs.
"U.S. Appl. No. 11/490,916, Examiner Interview Summary mailed Aug. 19, 2009", 2 pgs.
"U.S. Appl. No. 11/490,916, Final Office Action mailed Dec. 17, 2009", 11 pgs.
"U.S. Appl. No. 11/490,916, Non Final Office Action mailed May 5, 2009", 10 pgs.
"U.S. Appl. No. 11/490,916, Notice of Allowance mailed Jul. 9, 2010", 4 pgs.
"U.S. Appl. No. 11/490,916, Response filed Jan. 12, 2009 to Restriction Requirement Dec. 11, 2008", 7 pgs.
"U.S. Appl. No. 11/490,916, Response filed Apr. 15, 2010 to Final Office Action mailed Dec. 17, 2009", 12 pgs.
"U.S. Appl. No. 11/490,916, Response filed Sep. 3, 2009 to Non Final Office Action mailed May 5, 2009", 13 pgs.
"U.S. Appl. No. 11/490,916, Supplemental Notice of Allowability Mailed Oct. 14, 2010", 2 pgs.
"U.S. Appl. No. 11/511,152, Final Office Action mailed Aug. 10, 2009", 13 pgs.
"U.S. Appl. No. 11/511,152, Non-Final Office Action mailed Dec. 23, 2008", 14 pgs.
"U.S. Appl. No. 11/511,152, Non-Final Office Action mailed Dec. 30, 2009", 13 pgs.
"U.S. Appl. No. 11/511,152, Notice of Allowance mailed Jul. 28, 2010", 6 pgs.
"U.S. Appl. No. 11/511,152, Preliminary Amendment filed Oct. 17, 2006", 3 pgs.
"U.S. Appl. No. 11/511,152, Response filed Mar. 23, 2009 to Non Final Office Action mailed Dec. 23, 2008", 11 pgs.
"U.S. Appl. No. 11/511,152, Response filed Jun. 30, 2010 to Non-Final Office Action mailed Dec. 30, 2009", 12 pgs.
"U.S. Appl. No. 11/511,152, Response filed Nov. 12, 2009 to Final Office Action mailed Aug. 10, 2009", 13 pgs.
"U.S. Appl. No. 11/549,352, Appeal Brief filed Sep. 9, 2009", 36 pgs.
"U.S. Appl. No. 11/549,352, Examiner Interview Summary mailed Jun. 25, 2008", 2 pgs.
"U.S. Appl. No. 11/549,352, Examiner's Answer mailed Nov. 27, 2009 to Appeal Brief filed Sep. 9, 2009", 12 pgs.
"U.S. Appl. No. 11/549,352, Final Office Action mailed Mar. 9, 2009", 10 pgs.
"U.S. Appl. No. 11/549,352, Final Office Action mailed Aug. 26, 2008", 13 pgs.
"U.S. Appl. No. 11/549,352, Non-Final Office Action mailed Feb. 5, 2008", 11 pgs.
"U.S. Appl. No. 11/549,352, Notice of Panel Decision from Pre-Appeal Brief Review mailed Feb. 2, 2009", 2 pgs.
"U.S. Appl. No. 11/549,352, Pre-Appeal Brief for Review filed Dec. 20, 2008", 5 pgs.
"U.S. Appl. No. 11/549,352, Reply Brief filed Jan. 27, 2010", 8 pgs.
"U.S. Appl. No. 11/549,352, Response filed Jul. 7, 2008 to Non-Final Office Action mailed Feb. 5, 2008", 17 pgs.
"U.S. Appl. No. 11/549,352, Restriction Requirement mailed Aug. 12, 2013", 5 pgs.
"U.S. Appl. No. 11/683,577, Examiner Interview Summary mailed Jul. 7, 2009", 4 pgs.
"U.S. Appl. No. 11/683,577, Final Office Action mailed Nov. 9, 2009", 14 pgs.
"U.S. Appl. No. 11/683,577, Non-Final Office Action mailed Mar. 5, 2009", 13 pgs.
"U.S. Appl. No. 11/683,577, Notice of Allowance mailed Mar. 5, 2013", 11 pgs.
"U.S. Appl. No. 11/683,577, Response filed May 7, 2010 to Final Office Action mailed Nov. 9, 2009", 14 pgs.
"U.S. Appl. No. 11/683,577, Response filed Aug. 5, 2009 to Non Final Office Action mailed Mar. 5, 2009", 10 pgs.

(56) References Cited

OTHER PUBLICATIONS

"U.S. Appl. No. 11/683,584, Non-Final Office Action mailed Apr. 1, 2009", 9 pgs.
"U.S. Appl. No. 11/683,584, Examiner Interview Summary mailed Jul. 7, 2009", 4 pgs.
"U.S. Appl. No. 11/683,584, Final Office Action mailed Jan. 29, 2010", 9 pgs.
"U.S. Appl. No. 11/683,584, Notice of Allowance mailed Aug. 7, 2012", 6 pgs.
"U.S. Appl. No. 11/683,584, Preliminary Amendment filed Mar. 8, 2007", 1 pg.
"U.S. Appl. No. 11/683,584, Response filed Jul. 1, 2009 to Non Final Office Action mailed Apr. 1, 2009", 7 pgs.
"U.S. Appl. No. 11/683,584, Response filed Jul. 21, 2010 to Final Office Action mailed Jan. 29, 1010", 12 pgs.
"U.S. Appl. No. 11/745,070, Final Office Action mailed Dec. 11, 2009", 18 pgs.
"U.S. Appl. No. 11/745,070, Non Final Office Action mailed Apr. 27, 2009", 11 pgs.
"U.S. Appl. No. 11/745,070, Response filed Jul. 27, 2009 to Non Final Office Action mailed Apr. 27, 2009", 11 pgs.
"U.S. Appl. No. 11/745,105, Final Office Action mailed Mar. 30, 2010", 9 pgs.
"U.S. Appl. No. 11/745,105, Non Final Office Action mailed Feb. 7, 2012", 12 pgs.
"U.S. Appl. No. 11/745,105, Non Final Office Action mailed May 11, 2011", 13 pgs.
"U.S. Appl. No. 11/745,105, Non-Final Office Action mailed Sep. 18, 2009", 9 pgs.
"U.S. Appl. No. 11/745,105, Notice of Allowance mailed Aug. 20, 2012", 5 pgs.
"U.S. Appl. No. 11/745,105, Notice of Allowance mailed Oct. 31, 2011", 5 pgs.
"U.S. Appl. No. 11/745,105, Response filed Jan. 19, 2010 to Non Final Office Action mailed Sep. 18, 2009", 12 pgs.
"U.S. Appl. No. 11/745,105, Response filed Jun. 22, 2009 to Restriction Requirement mailed May 21, 2009", 6 pgs.
"U.S. Appl. No. 11/745,105, Response filed Jul. 29, 2010 to Final Office Action mailed Mar. 30, 2010", 12 pgs.
"U.S. Appl. No. 11/745,105, Response filed Aug. 6, 2012 to Non Final Office Action mailed Feb. 7, 2012", 11 pgs.
"U.S. Appl. No. 11/745,105, Response filed Sep. 12, 2011 to Non-Final Office Action mailed May 11, 2011", 13 pgs.
"U.S. Appl. No. 11/745,105, Restriction Requirement mailed May 21, 2009", 6 pgs.
"U.S. Appl. No. 11/854,844, Non Final Office Action mailed Jan. 11, 2013", 15 pgs.
"U.S. Appl. No. 11/854,844, Notice of Allowance mailed Sep. 27, 2013", 9 pgs.
"U.S. Appl. No. 11/854,844, Response filed May 13, 2013 to Non Final Office Action mailed Jan. 11, 2013", 15 pgs.
"U.S. Appl. No. 12/361,884, Advisory Action mailed Sep. 10, 2012", 3 pgs.
"U.S. Appl. No. 12/361,884, Examiner Interview Summary mailed Oct. 1, 2012", 3 pgs.
"U.S. Appl. No. 12/361,884, Final Office Action mailed Jul. 3, 2012", 17 pgs.
"U.S. Appl. No. 12/361,884, Non Final Office Action mailed Oct. 12, 2011", 15 pgs.
"U.S. Appl. No. 12/361,884, Notice of Allowance mailed Jan. 17, 2014", 7 pgs.
"U.S. Appl. No. 12/361,884, Notice of Allowance mailed Sep. 25, 2013", 10 pgs.
"U.S. Appl. No. 12/361,884, Preliminary Amendment filed Jun. 30, 2011", 12 pgs.
"U.S. Appl. No. 12/361,884, Response filed Apr. 12, 2012 to Non Final Office Action mailed Oct. 12, 2011", 21 pgs.
"U.S. Appl. No. 12/361,884, Response filed Aug. 28, 2012 to Final Office Action mailed Jul. 3, 2012", 18 pgs.
"U.S. Appl. No. 12/361,884, Response filed Oct. 3, 2012 to Final Office Action mailed Jul. 3, 2012", 18 pgs.
"U.S. Appl. No. 12/361,884, Supplemental Preliminary Amendment filed Jul. 27, 2011", 12 pgs.
"U.S. Appl. No. 12/365,428, Non Final Office Action mailed Aug. 31, 2011", 9 pgs.
"U.S. Appl. No. 12/365,428, Notice of Allowance mailed Feb. 22, 2012", 7 pgs.
"U.S. Appl. No. 12/365,428, Response filed Jan. 30, 2012 to Non Final Office Action mailed Aug. 31, 2011", 15 pgs.
"U.S. Appl. No. 12/910,106, Non Final Office Action mailed Apr. 4, 2011", 9 pgs.
"U.S. Appl. No. 12/910,106, Notice of Allowance mailed Jan. 26, 2012", 6 pgs.
"U.S. Appl. No. 12/910,106, Notice of Allowance mailed Oct. 27, 2011", 5 pgs.
"U.S. Appl. No. 12/910,106, Response filed Aug. 2, 2011 to Non-Final Office Action mailed Apr. 4, 2011", 14 pgs.
"U.S. Appl. No. 13/476,599, Examiner Interview Summary mailed Dec. 31, 2012", 3 pgs.
"U.S. Appl. No. 13/476,599, Final Office Action mailed Aug. 21, 2013", 8 pgs.
"U.S. Appl. No. 13/476,599, Non Final Office Action mailed Aug. 30, 2012", 6 pgs.
"U.S. Appl. No. 13/476,599, Response filed Dec. 19, 2012 to Non Final Office Action mailed Aug. 30, 2012", 11 pgs.
"U.S. Appl. No. 13/717,027 Preliminary Amendment Filed Jun. 25, 2013", 6 pgs.
"U.S. Appl. No. 13/929,286, Non Final Office Action mailed Dec. 11, 2013", 15 pgs.
"U.S. Appl. No. 13/929,286, Preliminary Amendment filed", 7 pgs.
"U.S. Appl. No. 14/044,094, Preliminary Amendment filed Oct. 28, 2013", 8 pgs.
"U.S. Appl. No. 11/549,352, Appeal Decision mailed Jul. 17, 12", 9 pgs.
"European Application Serial No. 05815206.7, Communication Dec. 18, 2009", 4 pgs.
"European Application Serial No. 05815206.7, Office Action mailed May 16, 2012", 5 pgs.
"European Application Serial No. 05815206.7, Office Action mailed Sep. 12, 2012", 27 pgs.
"European Application Serial No. 05815206.7, Response filed Apr. 19, 2010 to Communication Dec. 18, 2009", 27 pgs.
"European Application Serial No. 05815215.8, Communication mailed Dec. 18, 2009", 2 pgs.
"European Application Serial No. 05815215.8, Response filed Mar. 19, 2010 to Communication mailed Dec. 18, 2009", 12 pgs.
"European Application Serial No. 05817448.3, Communication mailed Dec. 18, 2009", 2 pgs.
"European Application Serial No. 05817448.3, Office Action mailed May 16, 2012", 5 pgs.
"European Application Serial No. 05817448,3, Response filed Mar. 19, 2010 to Communication mailed Dec. 18, 2009", 9 pgs.
"European Application Serial No. 05817448.3, Response filed Sep. 14, 2012 to Office Action mailed May 16, 2012", 14 pgs.
"European Application Serial No. 06790023.3, Office Action Mailed Mar. 4, 2009", 6 pgs.
"European Application Serial No. 06790023.3, Office Action mailed Jul. 26, 2008", 2 pgs.
"European Application Serial No. 06790023.3, Response filed Aug. 20, 2008 to Office Action mailed Jul. 16, 2008", 17 pgs.
"European Application Serial No. 06790023.3, Response filed Sep. 14, 2009 to Office Action Mailed Mar. 4, 2009", 11 pgs.
"European Application Serial No. 06825988.6, Office Action mailed Mar. 4, 2009,", 7 pgs.
"European Application Serial No. 06825988.6, Office Action mailed Jul. 16, 2008", 2 pgs.
"European Application Serial No. 06825988,6, Response filed Aug. 20, 2008 to Office Action mailed Jul. 16, 2008", 26 pgs.
"European Application Serial No. 06825988.6, Response filed Sep. 14, 2009 to Office Action mailed Mar. 4, 2009.", 12 pgs.
"European Application Serial No. 06847612.6, Office Action mailed May 26, 2009", 3 pgs.

(56) References Cited

OTHER PUBLICATIONS

"European Application Serial No. 06847612.6, Office Action mailed Jul. 30, 2008", 2 pgs.
"European Application Serial No. 06847612.6, Office Action mailed Dec. 7, 2010", 4 pgs.
"European Application Serial No. 06847612.6, Response filed Apr. 12, 2011 to Office Action mailed Dec. 7, 2010", 5 pgs.
"European Application Serial No. 06847612.6, Response filed Sep. 9, 2008 to Office Action mailed Jul. 30, 2008", 4 pgs.
"European Application Serial No. 06847612.6, Response filed Oct. 26, 2009 to Office Action mailed May 26, 2009", 12 pgs.
"European Application Serial No. 06847612.6, Summons to Attend Oral Proceedings mailed Jun. 20, 2012", 3 pgs.
"European Application Serial No. 07759589.0, Office Action mailed Jan. 29, 2009", 3 pgs.
"European Application Serial No. 07759589.0, Office Action Mailed Feb. 18, 2010", 3 pgs.
"European Application Serial No. 07759589.0, Response filed Jun. 24, 2010 to Office Action mailed Feb. 18, 2010", 6 pgs.
"European Application Serial No. 07759589.0, Summons to Attend Oral Proceedings mailed May 17, 2011", 3 pgs.
"European Application Serial No. 07759589.0, Written Submission filed Dec. 5, 2011 to Summons to Attend Oral Proceedings dated May 17, 2011", 16 pgs.
"European Application Serial No. 09709347.0, Office Action mailed Oct. 4, 2010", 1 pg.
"European Application Serial No. 09709347.0, Response filed Oct. 28, 2010 to Office Action mailed Oct. 4, 2010", 7 pgs.
"International Application Serial No. PCT/US2005/037977, International Preliminary Report on Patentability dated Apr. 24, 2007", 9 pgs.
"International Application Serial No. PCT/US2005/037977, International Search Report mailed Mar. 21, 2006", 4 pgs.
"International Application Serial No. PCT/US2005/037979, Written Opinion mailed Mar. 21, 2008", 8 pgs.
"International Application Serial No. PCT/US2005/037978, International Preliminary Report on Patentability dated Apr. 24, 2007", 13 pgs.
"International Application Serial No. PCT/US2005/037978, International Search Report mailed Jun. 13, 2006", 5 pgs.
"International Application Serial No. PCT/US2005/037978, Written Opinion mailed Jun. 13, 2006", 12 pgs.
"International Application Serial No. PCT/US2005/037979, International Preliminary Report on Patentability dated Apr. 24, 2007", 9 pgs.
"International Application Serial No. PCT/US2005/037979, International Search Report mailed Mar. 21, 2006", 4 pgs.
"International Application Serial No. PCT/US2005/037979, Written Opinion mailed Mar. 21, 2006", 8 pgs.
"International Application Serial No. PCT/US2006/033414, International Preliminary Report on Patentability mailed Jun. 19, 2008", 11 pgs.
"International Application Serial No. PCT/US2006/033414, International Search Report mailed Mar. 1, 2007", 5 pgs.
"International Application Serial No. PCT/US2006/033414, Written Opinion mailed Mar. 1, 2007", 9 pgs.
"International Application Serial No. PCT/US2006/040291, International Preliminary Report on Patentability mailed Jun. 19, 2008", 11 pgs.
"International Application Serial No. PCT/US2006/040291, Search Report mailed Apr. 4, 2007", 5 pgs.
"International Application Serial No. PCT/US2006/040291, Written Opinion mailed Apr. 4, 2007", 9 pgs.
"International Application Serial No. PCT/US2006/047553, International Preliminary Report on Patentability mailed Jul. 3, 2008", 8 pgs.
"International Application Serial No. PCT/US2006/047553, International Search Report rnailed Jun. 20, 2007", 3 pgs.
"International Application Serial No. PCT/US2006/047553, Written Opinion mailed Jun. 20, 2007", 6 pgs.
"International Application Serial No. PCT/US2007/085376, International Preliminary Report on Patentability mailed Oct. 9, 2008", 10 pgs.
"International Application Serial No. PCT/US2007/065376, International Search Report mailed Dec. 14, 2007", 5 pgs.
"International Application Serial No. PCT/US2007/065376, Written Opinion mailed Dec. 14, 2007", 11 pgs.
"International Application Serial No. PCT/US2007/074125, International Preliminary Report on Patentability mailed Feb. 5, 2009", 9 pgs.
"International Application Serial No. PCT/US2007/074125, International Search Report mailed Dec. 6, 2007", 4 pgs.
"International Application Serial No. PCT/US2007/074125, Writen Opinion mailed Dec. 6, 2007", 8 pgs.
"International Application Serial No. PCT/US2007/074135, International Preliminary Report on Patentability mailed Feb. 5, 2009", 9 pgs.
"International Application Serial No. PCT/US2007/074135, International Search Report mailed Nov. 6, 2007", 4 pgs.
"International Application Serial No. PCT/US2007/074135, Written Opinion mailed Nov. 6, 2007", 8 pgs.
"International Application Serial No. PCT/US2007/078405, International Preliminary Report on Patentability mailed Mar. 26, 2009", 9 pgs.
"International Application Serial No. PCT/US2007/078405, International Search Report mailed May 20, 2008", p. 220, 7 pgs.
"International Application Serial No. PCT/US2007/078405, Written Opinion mailed May 20, 2008", p. 237, 7 pgs.
"International application serial No. PCT/US2009/000587 Written Opinion mailed Apr. 24, 2009", 8 pgs.
"International Application Serial No. PCT/US2009/000587, International Preliminary Report on Patentability mailed Aug. 19, 2010", 10 pgs.
"International Application Serial No. PCT/US2009/000587, International Search Report mailed Apr. 24, 2009", 7 pgs.
"International Application Serial No. PCT/US2007/000693, International Preliminary Report on Patentability mailed Aug. 19, 2010", 9 pgs.
"International Application Serial No. PCT/US2009/000693, International Search Report mailed May 8, 2009", 5 pgs.
"International Application Serial No. PCT/US2009/000693, Written Opinion mailed May 8, 2009", 8 pgs.
"Japanese Application Serial No. 2007-538087, Office Action mailed Apr. 11, 2011", (w/ English Translation), 5 pgs.
"Japanese Application Serial No. 2007-538087, Office Action mailed Apr. 17, 2012", w/ English Translation, 8 pgs.
"Japanese Application Serial No. 2007-538087, Office Action mailed Oct. 5, 2011", (w/ English Translation), 14 pgs.
"Japanese Application Serial No. 2007-538087, Response filed Mar. 23, 2012 to Office Action mailed Oct. 5, 2011", (w/ English Translation of Claims), 9 pgs.
"Japanese Application Serial No. 2007-538087, Response filed Jun. 27, 2011 to Office Action dated Apr. 11, 2011", (w/ English Translation of Amended Claims), 12 pgs.
"Japanese Application Serial No. 2007-538087, Response filed Jul. 13, 2012 to Office Action mailed Apr. 17, 2012", (w/ English Translation of Amended Claims), 13 pgs.
"Japanese Application Serial No. 2007-538088, Notice of Final Rejection mailed Dec. 6, 2011", (w/ English Translation), 9 pgs.
"Japanese Application Serial No. 2007-538088, Office Action mailed Jun. 13, 2011", (w/ English Translation), 5 pgs.
"Japanese Application Serial No. 2007-538088, Response filed Mar. 27, 2012 to Final Office Action mailed Dec. 6, 2011", (w/ English Translation of Claims), 11 pgs.
"Japanese Application Serial No. 2007-538088, Response filed Aug. 25, 2011 to Office Action dated Jun. 13, 2011", (w/ English Translation of Amended Claims), 9 pgs.
"Japanese Application Serial No. 2007-538089, Office Action mailed Mar. 3, 2011", (w/ English Translation), 6 pgs.
"Japanese Application Serial No. 2007-538089, Response filed May 25, 2011 to Office Action mailed Mar. 3, 2011", (w/ English Translation of Amended Claims), 8 pgs.

(56) References Cited

OTHER PUBLICATIONS

"Japanese Application Serial No. 2008-544324, Office Action mailed May 22, 2012", (w/ English.Translation), 5 pgs.
"Japanese Application Serial No. 2008-544324, Office Action mailed Nov. 22, 2011", (w/ English Translation), 5 pgs.
"Japanese Application Serial No. 2008-544324, Response filed Jan. 27, 2012", (w/ English Translation of Amended Claims), 10 pgs.
"Japanese Application Serial No. 2008-544332, Office Action mailed Nov. 29, 2011", (w/ English Translation), 5 pgs.
"Japanese Application Serial No. 2008-544332, Response filed Mar. 19, 2012 to Office Action mailed Nov. 29, 2011", (w/ English Translation of Claims), 9 pgs.
"Japanese Application Serial No. 2009-503252, Office Action mailed Mar. 21, 2012", (w/ English Translation), 9 pgs.
"Japanese Application Serial No. 2009-503252, Response filed Jun. 20, 2012 to Office Action mailed Mar. 21, 2012", (w/ English Claims), 9 pgs.
"Japanese Application Serial No. 2010-545866, Office Action mailed Jun. 5, 2012", (w/ English Translation), 5 pgs.
"Japanese Application Serial No. 2010-545866, Response filed Sep. 5, 2012 to Office Action mailed Jun. 5, 2012", (w/ English Translation of Amended Claims), 12 pgs.

"Telemetry Research Transcutaneous Energy Transfer (TET) Technology Summary", Telemetry Research Ltd., www.telemetryresearch.com, (No date listed), 1 pg.
Busch, M., et al., "On the Heating of Inductively Coupled Resonators (Stents) During MRI Examinations", Magnetic Resonance in Medicine, 54, (2005), 775-785.
Manoharan, G., et al., "Novel passive implantable atrial defibrillator using transcutaneous radiofrequency energy transmission successfully cardioverts atrial fibrillation.", Circulation, 108(11), (Sep. 16, 2003), 1382-8.
Piella, J. P., "Energy management, wireless and system solutions for highly integrated implantable devices", Doctoral Thesis by Jordi Parrarnon I Piella for the Universitat Autonoma de Barcelona, certified Dec. 2001, 62 pgs.
Si, Ping, et al., "A Frequency Control Method for Regulating Wireless Power to Implantable Devices", IEEE Transactions on Biomedical Circuits and Systems, 2(1), (Mar. 2008), 22-29.
Swain, E., "Breakthrough Products Could Put Lesser-Known Firms on the map", MDDI, (Apr. 2004), 6 pgs.
Wagner, Brian K, "Electrodes, Leads, and Biocompatibility", Chapter 6—Design of Cardiac Pacemakers, edited by John G. Webster., (1995), 133-160.

\* cited by examiner

WIRELESS TISSUE ELECTROSTIMULATION

CLAIM OF PRIORITY

This patent application is a continuation of U.S. application Ser. No. 12/361,884, filed on Jan. 29, 2009 (published as US 2009/0204170 and U.S. Pat. No. 8,738,147), which claims the benefit of priority, under 35 U.S.C. Section 119(e), to Roger Hastings et al., U.S. Provisional Patent Application Ser. No. 61/063,876, entitled "WIRELESS STENT ELECTROSTIMULATION SYSTEM," filed on Feb. 7, 2008, both of which are incorporated herein by reference in its entirety.

This patent application also claims the benefit of priority, under 35 U.S.C. Section 119(e), to Roger Hastings et al., U.S. Provisional Patent Application Ser. No. 61/059,993, entitled "WIRELESS TISSUE ELECTROSTIMULATION SYSTEM," filed on Jun. 9, 2008, incorporated herein by reference in its entirety.

CROSS-REFERENCE TO RELATED PATENT DOCUMENTS

This patent application is related to U.S. patent application Ser. No. 11/854,844, entitled "Cardiac Stimulation Using Leadless Electrode Assemblies," filed on Sep. 13, 2007, now issued as U.S. Pat. No. 8,644,934, and U.S. patent application Ser. No. 11/511,152, entitled "Cardiac Stimulation System," filed on Aug. 28, 2006, now issued as U.S. Pat. No. 7,848,823, the entire contents of both of which are incorporated herein by reference.

BACKGROUND

A variety of therapeutically-useful intra-body electrostimulation techniques have been employed by physicians to treat both acute and chronic patient conditions. Electrostimulation of soft muscle tissue may be used, for instance, to elicit contractile behavior, or to inhibit such contractile activation.

In particular, electrostimulation is commonly used for cardiac rhythm management. Cardiac rhythm management devices include, for example, pacemakers, cardiac re-synchronization therapy devices, and cardioverter defibrillators. Cardiac rhythm management devices can be used to treat conditions such as atrial or ventricular tachycardia, atrial or ventricular fibrillation, bradycardia, and congestive heart failure.

An example of an application of a cardiac rhythm management device includes a battery-operated pulse-generator assembly subcutaneously implanted in the pectoral region, connected to one or more implantable leads deployed through the vasculature using a catheter-based delivery system to locations either within one or more of the heart chambers, or within one of the great veins of the heart.

Implantable flexible leads include one or more exposed electrodes to directly stimulate cardiac tissue, or to sense potentials developed across the electrodes by the tissue (e.g., for sensing intrinsic cardiac activity, or sensing the evoked response to the application of electrostimulus). Tissue growth occurs, and frequently surrounds the area of the electrode in contact with tissue. This may result in the beneficial effect of reducing the required electrostimulus threshold to achieve the desired response, but also presents challenges should the necessity arise to re-position or remove the lead. This may preclude the usage of multiple leads in certain locations.

Epicardial stimulus locations are also sometimes used, for instance during times when acute pacing therapy is desired, associated with other medical procedures, and where access is easily obtained to the pericardial cavity.

OVERVIEW

Some conditions, such as congestive heart failure, benefit from pacing at multiple cardiac sites in a specially timed manner, including pacing at a right-ventricular site, and one or more left-ventricular sites.

Generally, leads are contra-indicated in the left heart chambers due to the risk of thrombo-embolism. Also, risk exists of mechanical dislodgement, due to the more significant motions, acceleration and impingement of cardiac tissue on the lead and electrode assembly, if a lead system is implanted endocardially in the left ventricle or left atrium.

For the reasons above, left-ventricular pacing is typically accomplished from a venous site. However, the risk of obstructing a significant proportion of the venous cross section is great, compromising blood supply to myocardium. It can be difficult to pace at more than one left ventricular site. Additionally, the efficiency of pacing at a venous site can be correspondingly less desirable than an intra-chamber location such as the left-ventricular free wall (e.g., the required pacing energy level to elicit reliable activation or "capture," can be higher at the venous site than at a corresponding endocardial location wherein the electrode is directly implanted in the myocardium). The complexity of lead removal and the limited available area can preclude the usage of multiple leads to achieve multiple stimulation sites in the left heart.

Wireless pacing electrodes can eliminate the need for the wired connection between the pulse generator assembly and an electrode assembly at a pacing site, since such wireless assemblies can fit entirely within a heart chamber, at an endocardial location. Generally, pacing energy is supplied to the tissue from a tiny rechargeable battery located in the body of the wireless pacing electrode. Such a design has the advantage of enabling an autonomous pacing assembly, but size considerations can result in frequent (e.g., daily) battery recharge via magnetic induction. Further, the construction of various wireless pacing devices using materials with high magnetic permeability, such as ferrite-core inductors, can present a compatibility problem with magnetic resonance imaging (MRI) equipment.

By contrast, among other things, the present system in certain examples can provide electrostimulation at patient implant locations, such as an endocardial location, where usage of lead-wire systems is problematic, and wherein stimulation is desired at multiple sites separate and distinct from the location of a therapy control unit and wireless energy source.

The present system in certain examples can also improve useful wireless communication range to, for example, several centimeters in cardiac pacing or other electrostimulation applications, using one or more inductors including a core material having a lower relative magnetic permeability than ferrite, or substantially equal to 1 (e.g., such as air, body tissue, bodily fluids, or one or more other media), or using a tuned receiver design. Multiple receivers can be driven by a single inductive transmit antenna with limited loss in efficiency, as compared to a single receiver.

The inductive transmit antenna can be located either subcutaneously within the patient or included with an external device, such as a hospital bed, operating table, hand-held device, hat or clothing, for example.

In the case of a subcutaneously-implanted therapy control unit and inductive transmitter (such as a cardiac rhythm management device), explant might be required to replace the battery. Enhanced efficiency from resonant coupling or larger air-core loop inductive antenna structures can facilitate increased operating time between recharge operations or battery replacement.

In the case of an external inductive transmitter, a greater distance between the transmitter and wireless electrostimulation node "seed" devices can be achieved.

The wireless electrostimulation node "seed" device can be implanted at a cardiac location, such as endocardially, entirely within a heart chamber, and can be configured with an expandable inductive loop antenna. During the implantation procedure, the expandable loop can be initially collapsed or folded to allow easier implant, and then unfolded or expanded to achieve a larger surface area, and hence greater coupling to the inductive transmit antenna. In a cardiac pacing example, an inductive transmit antenna can be incorporated into a cardiac lead system and can be configured to expand or unfold once implanted in a desired location.

In an example, a wireless electrostimulation system can include a wireless energy transmission source, and an implantable cardiovascular wireless electrostimulation node. In an example, a receiver circuit can include an inductive antenna, and the antenna can be configured to capture magnetic energy to generate a tissue electrostimulation. In an example, a tissue electrostimulation circuit, coupled to the receiver circuit, can be configured to deliver energy captured by the receiver circuit as a tissue electrostimulation waveform, without requiring a discrete capacitor or electrochemical storage (e.g., a battery, a capacitor using bodily fluid or tissue as an electrolyte, or one or more other storage devices) on-board or conductively coupled to the receiver circuit. In an example, delivery of tissue electrostimulation can be initiated by a therapy control unit.

Example 1 comprises a wireless electrostimulation system. In this example, the system includes: a wireless energy transmission source, including an inductive antenna, configured to generate a time-varying magnetic flux; a cardiovascular wireless electrostimulation node sized and shaped to be implantable using a percutaneous transluminal catheter delivery system, the wireless electrostimulation node comprising: a receiver circuit configured to capture at least enough inductively-coupled energy from the inductive antenna to generate a tissue electrostimulation, the receiver circuit comprising a mechanically-expandable inductive pickup configured to link the time-varying magnetic flux, the inductive pickup comprising a core material including a relative magnetic permeability less than 1.1; a tissue electrostimulation circuit, coupled to the receiver circuit, configured to deliver energy captured by the receiver circuit as a specified tissue electrostimulation waveform, the tissue electrostimulation circuit comprising at least one tissue electrostimulation electrode; and a therapy control unit, communicatively coupled to the tissue electrostimulation node and configured to initiate a delivery of a tissue electrostimulation by the tissue electrostimulation electrode.

In Example 2, the system of Example 1 optionally comprises a system wherein the cardiovascular wireless electrostimulation node is configured and sized for intravascular delivery.

In Example 3, the system of at least one of Examples 1-2 optionally comprises a system wherein the receiver circuit comprises: an energy storage device configured to store inductively-coupled energy transferred by the time-varying magnetic flux; wherein the energy storage device is configured to store at most 1 milliJoule of energy; and wherein the tissue electrostimulation is inhibited by a depletion of the energy storage device no more than 1 minute after the termination of the inductively-coupled energy transfer.

In Example 4, the system of at least one of Examples 1-3 optionally comprises a system wherein the tissue electrostimulation circuit comprises: a rectifier, coupled between the receiver circuit and the tissue stimulation electrode; a direct-current blocking device, coupled between the tissue electrostimulation electrode and the receiver circuit; wherein the at least one tissue electrostimulation electrode comprises a cathode configured to be coupled to cardiac tissue; wherein the at least one tissue electrostimulation electrode comprises an anode configured to be coupled to cardiac tissue; and wherein the tissue electrostimulation circuit is configured to be capable of generating, between the anode and the cathode, an electrostimulation pulse of at least 2.5V peak amplitude at a pulse width of 0.4 msec when coupled to a 500 Ohm equivalent load.

In Example 5, the system of at least one of Examples 1-4 optionally comprises: a mechanically-expandable inductive pickup comprising: an insulated wire loop; an expandable mechanical support comprising a loop of shape-memory material mechanically coupled to the insulated wire loop, wherein at least a portion of the loop of shape-memory material is non-conductive; a housing comprising: a receiver circuit electrical charge storage device conductively coupled to the insulated wire loop; the tissue electrostimulation circuit; wherein the housing is disposed within a space encompassed by the loop of shape-memory material; and a strut, comprised of shape-memory material, configured to secure the loop of shape-memory material to the cylindrical housing.

In Example 6, the system of at least one of Examples 1-5 optionally comprises a bio-compatible dielectric encapsulant configured to encompass at least a portion of the inductive pickup.

In Example 7, the system of at least one of Examples 1-6 optionally comprises a system wherein the wireless energy transmission source is configured to vary a burst pulse duration of the time-varying magnetic flux, wherein the tissue electrostimulation circuit comprises a voltage clamping device coupled to the output of the rectifier, and wherein the energy content of the electrostimulation pulse is controlled by the burst pulse duration when a voltage across the voltage clamping device is substantially equal to or greater than a voltage clamping device threshold voltage.

In Example 8, the system of at least one of Examples 1-7 optionally comprises a system wherein the inductive pickup is configured for a maximum outside diameter, when expanded, of less than or equal to 2 cm; wherein the housing comprises a cylindrical diameter less than or equal to 2 mm, and a length less than or equal to 5 mm; and wherein a total length of the cylindrical housing and the cardiac tissue attachment mechanism is less than or equal to a nominal minimum myocardial tissue wall thickness of 10 mm.

In Example 9, the system of at least one of Examples 1-8 optionally comprises a system wherein the wireless energy transmission source is configured to generate the time-varying magnetic flux at a specified receiver resonant frequency within a range of frequencies from 500 kilohertz to 5 megahertz, inclusive; and wherein the wireless energy transmission source is configured to deliver the inductively coupled energy at a power coupling efficiency of at least 1%.

In Example 10, the system of at least one of Examples 1-9 optionally comprises a system wherein the wireless energy transmission source and the therapy control unit are both configured to be located external to a patient's body containing the wireless electrostimulation node.

In Example 1, the system of at least one of Examples 1-10 optionally comprises a battery-powered implantable cardiac rhythm management unit that includes the wireless energy transmission source and the therapy control unit.

In Example 12, the system of at least one of Examples 1-11 optionally comprises a system wherein the wireless energy transmission source comprises: an implantable flexible lead comprising: a distal end configured to be located near the implantable wireless electrostimulation node; a proximal end configured to be located at or near a housing of the battery-powered implantable cardiac rhythm management unit; at least two antenna feed conductors disposed internally to the lead and conductively coupled to the housing of the battery-powered implantable cardiac rhythm management unit; the inductive antenna disposed at the distal end of the lead, and conductively coupled to the at least two antenna feed conductors at the distal end of the lead; and the therapy control unit configured to energize the at least two antenna feed conductors.

Example 13 describes a method. In this example, the method comprises: delivering a cardiovascular wireless electrostimulation node to an intra-body location; expanding a wireless electrostimulation node inductive pickup; generating a time-varying magnetic flux; linking the time-varying magnetic flux to the wireless electrostimulation node inductive pickup; configuring a wireless electrostimulation node inductive pickup wire loop with a core material of a relative magnetic permeability less than 1.1; capturing at least enough inductively-coupled energy to deliver a tissue electrostimulation; controlling the initiation of the delivery of a specified tissue electrostimulation waveform; and delivering a specified tissue electrostimulation waveform in response to an initiation.

In Example 14, the method of Example 13 optionally comprises delivering a cardiovascular wireless electrostimulation node through a vascular path to an intra-body location.

In Example 15, the method of at least one of Examples 13-14 optionally comprises: storing the inductively-coupled energy within an energy storage device included in the wireless electrostimulation node; inhibiting the storage of more than 1 milliJoule of energy within the energy storage device; terminating the time-varying magnetic flux; depleting the energy storage device; and inhibiting the delivery of the tissue electrostimulation more than 1 minute after the termination of the time-varying magnetic flux in response to the depleting the energy storage device.

In Example 16, the method of at least one of Examples 13-15 optionally comprises: rectifying the time-varying magnetic flux; coupling a cathode to cardiac tissue; coupling an anode to cardiac tissue; generating, between the anode and the cathode, an electrostimulation pulse of at least 2.5V peak amplitude at a pulse width of 0.4 msec when coupled to a 500 Ohm equivalent load; and blocking the passage of direct-current between a tissue stimulation electrode and a receiver circuit.

In Example 17, the method of at least one of Examples 13-16 optionally comprises: insulating the inductive pickup wire loop; coupling the inductive pickup wire loop to a shape-memory mechanical support mechanically; expanding the shape-memory expandable mechanical support to a specified loop shape proximate to a cardiac tissue wall; forming a non-conductive portion along the circumference of the shape-memory expandable mechanical support; coupling the shape-memory mechanical support to a cylindrical housing mechanically; and disposing the cylindrical housing within a space encompassed by the shape-memory mechanical support.

In Example 18, the method of at least one of Examples 13-17 optionally comprises: encompassing at least a portion of the inductive pickup with a bio-compatible dielectric encapsulant.

In Example 19, the method of at least one of Examples 13-18 optionally comprises: varying a burst pulse duration of the time-varying magnetic flux; clamping a voltage developed by the rectifying the time-varying magnetic flux; and controlling the energy content of the electrostimulation pulse, via the varying of the burst pulse duration of the time-varying magnetic flux, when a voltage across a voltage clamping device is substantially equal to or greater than a voltage clamping device threshold voltage.

In Example 20, the method of at least one of Examples 13-19 optionally comprises: expanding the inductive pickup to a maximum outside diameter, when expanded, of less than or equal to 2 cm; limiting the cylindrical housing to a diameter less than or equal to 2 mm; limiting the cylindrical housing to a length less than or equal to 5 mm; and limiting a total length of the cylindrical housing and a cardiac tissue attachment mechanism to less than or equal to a nominal minimum myocardial tissue wall thickness of 10 mm.

In Example 21, the method of at least one of Examples 13-20 optionally comprises: generating the time-varying magnetic flux at a specified receiver resonant frequency within a range of frequencies from 500 kilohertz to 5 megahertz, inclusive; and transferring the inductively-coupled energy at a power coupling efficiency of at least 1%.

In Example 22, the method of at least one of Examples 13-21 optionally comprises: generating the time-varying magnetic flux from a location external to a patient's body; and initiating a tissue electrostimulation from a location external to the patient's body.

In Example 23, the method of at least one of Examples 13-22 optionally comprises: delivering a battery-powered implantable cardiac rhythm management unit to an intra-body location; conductively coupling an inductive antenna to the implantable cardiac rhythm management device; generating the time-varying magnetic flux using the inductive antenna; and initiating a tissue electrostimulation using the implantable cardiac rhythm management unit.

In Example 24, the method of at least one of Examples 13-23 optionally comprises: locating a distal end of an implantable flexible lead near to the implantable wireless electrostimulation node; mechanically coupling the inductive antenna to the distal end of the implantable flexible lead; locating a proximal end of the cardiovascular implantable flexible lead at or near to a housing of the battery-powered implantable cardiac rhythm management unit therapy control unit; locating at least two antenna feed conductors within the implantable flexible lead; conductively coupling the at least two antenna feed conductors from the battery-powered implantable cardiac rhythm management unit therapy control unit housing to the inductive antenna; and energizing the at least two antenna feed conductors.

Example 25 describes a system. In this example, the system comprises: means for delivering a cardiovascular wireless electrostimulation node to an intra-body location; means for expanding a wireless electrostimulation node inductive pickup; means for generating a time-varying magnetic flux; means for linking the time-varying magnetic flux to the wireless electrostimulation node inductive pickup; means for surrounding a wireless electrostimulation node inductive pickup wire loop with a material of a relative magnetic permeability less than 1.1; means for capturing at least enough inductively-coupled energy to deliver a tissue electrostimulation;

means for controlling the initiation of the delivery of a specified tissue electrostimulation waveform; and means for delivering a specified tissue electrostimulation waveform in response to an initiation.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
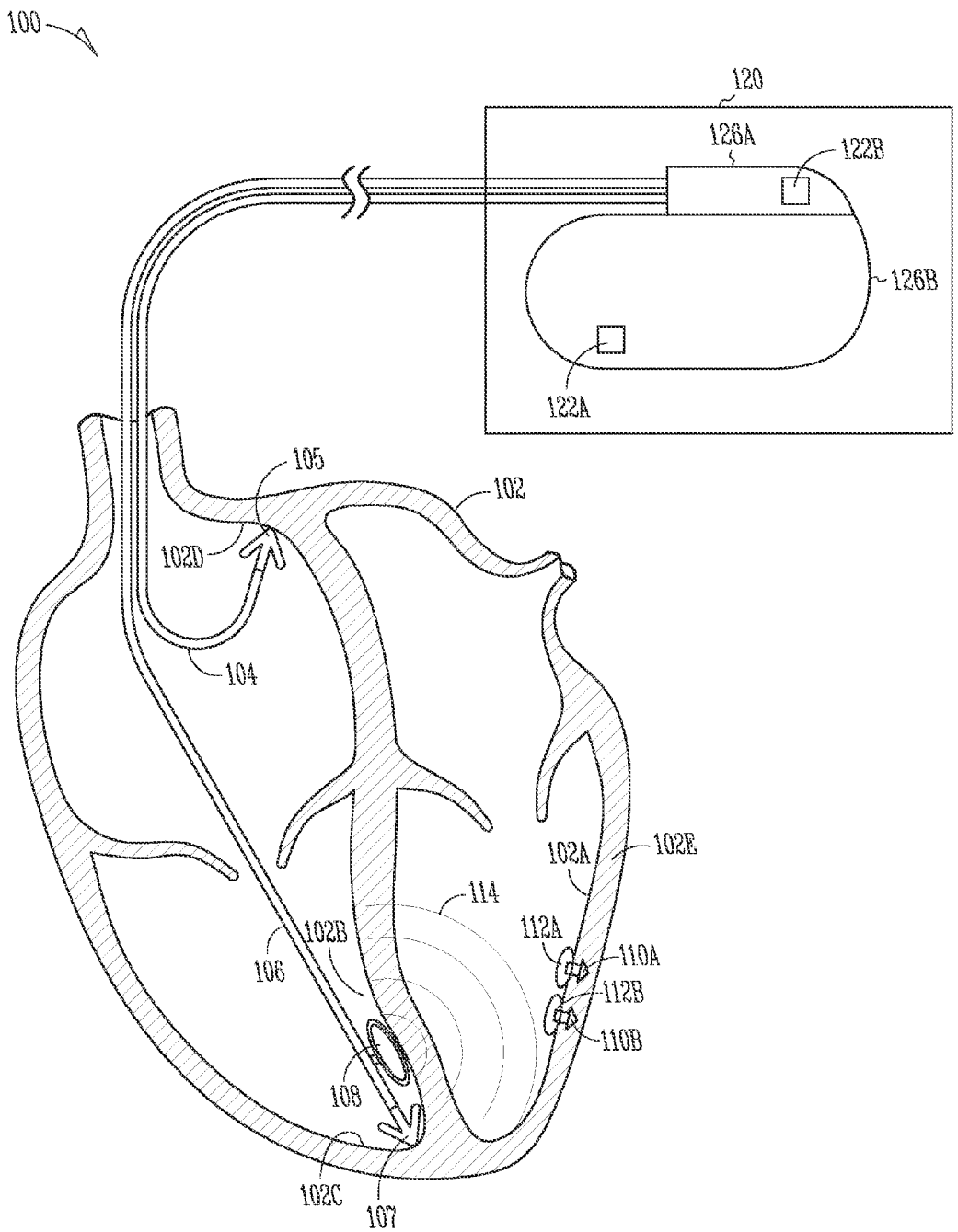
FIG. 1 is a diagram illustrating generally an example of at least a portion of a wireless electrostimulation system including a wireless energy transmission source, an implantable flexible lead comprising an inductive antenna, and multiple wireless electrostimulation nodes configured at cardiac sites.

FIG. 1 is a diagram illustrating generally an example of at least a portion of a wireless electrostimulation system 100 including a subcutaneous implantable cardiac rhythm management unit 120, and an implantable flexible lead 106 coupled to an inductive antenna 108, and multiple implantable wireless electrostimulation nodes 110A, 110B. FIGS. 3A-B, 4A-B can be referred to for more detailed views of examples of wireless electrostimulation nodes 110A, 110B.

The implantable wireless electrostimulation nodes, 110A, 110B, can be implanted entirely within the heart, for example, at an endocardial site along the left ventricular free wall 102A and penetrating the myocardium 102E. In the example of FIG. 1, the combination of the cardiac rhythm management unit 120, flexible lead 106, and inductive antenna 108 can be configured as a wireless energy transmission source.

The wireless electrostimulation nodes or "seeds," 110A, 110B, can be configured to receive inductively-coupled electromagnetic energy 114 as a time-varying flux generated by the inductive antenna 108. The energy 114 is captured by expandable inductive pickups 112A, 112B coupled to each seed 110A, 110B.

In the example shown in FIG. 1, the inductive antenna 108 can be disposed at the distal end of the implantable flexible lead 106 such as to transmit energy 114 across the ventricular septal region 102B, with the antenna 108 located near a fixation device 107. The fixation device 107 can be located at or near the apical region 102C of the right ventricle.

In an example, the implantable flexible lead 106 can be configured with at least two internal antenna feed conductors. The antenna feed conductors can be electrically coupled to an implantable cardiac rhythm management (CRM) device 120 through a header block 126A. The header block 126A can be used to mechanically and electrically couple one or more leads such as 104, 106 to, for example, electronics, control circuitry, or a battery located within the cardiac rhythm management device 120 therapy control unit housing 126B.

The CRM device 120 can be configured to wirelessly control initiation or timing of electrostimulation via wireless seeds 110A, 110B. The CRM device 120 can also be configured to generate energy 114 and to wirelessly communicate energy to the wireless seeds 110A, 110B such as for use in providing electrostimulation. In certain examples, the CRM device 120 can also provide electrostimulation to one or more cardiac sites, such as near 102B, 102C, 102D, such as by using one or more tissue attachment or fixation devices 105, 107 respectively comprising one or more conductive electrodes. The electrodes can be conductively supplied with electrostimulation energy, such as through one or more wires located internally to one or more of leads 104, 106.

Figure 10:
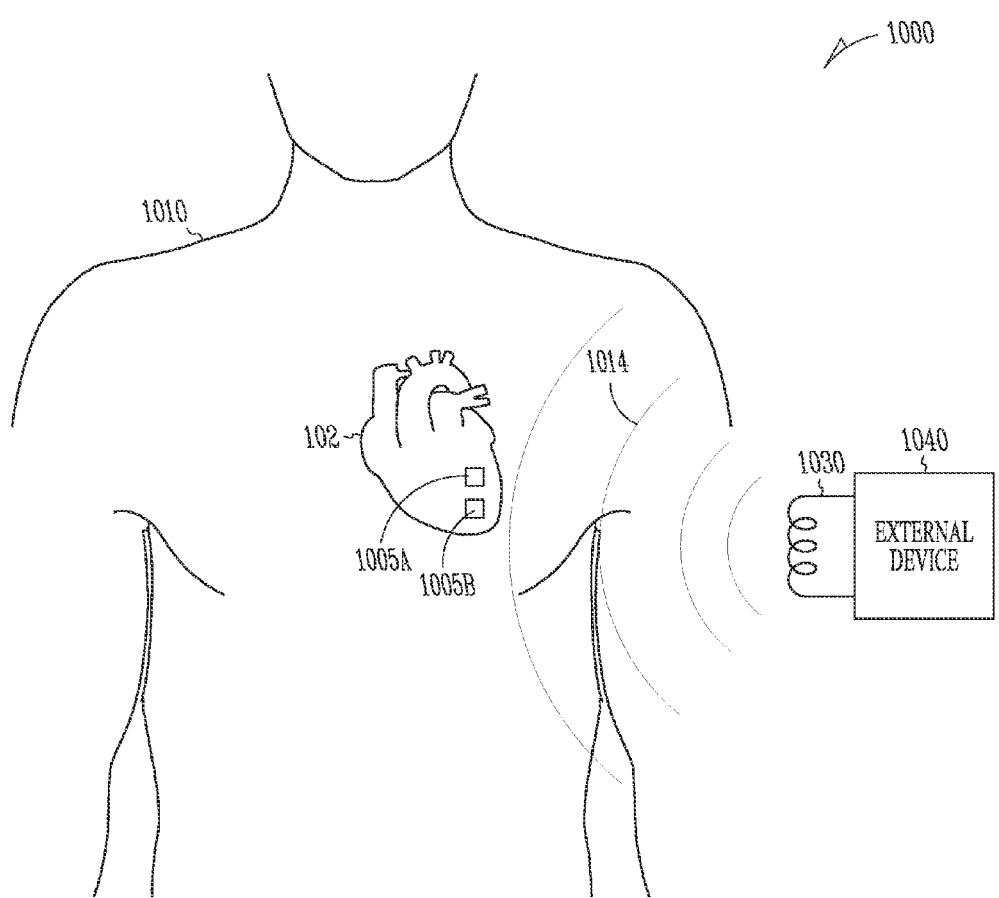
FIG. 10 is a diagram, similar to FIG. 1, but illustrating generally an example of at least a portion of a wireless electrostimulation system including an external device generating a time-varying magnetic flux.

In certain examples, one or more additional wireless stimulation nodes, such as 110A, 110B can be located in one or more other left heart 102 regions, such as the left atrium or left ventricular septal region. Such locations within or associated with the left heart 102 can be used, for example, in delivery of electrostimulation such as for cardiac resynchronization therapy, or to achieve conversion of atrial or ventricular tachyarrhythmias through electrostimulation. In examples involving one or more left-atrially associated seeds, similar to 110A, 110B, a right-atrial flexible implantable lead 104, and fixation device 105 can incorporate an inductive antenna 108, such as located in the atrial septal region, or one or more other atrial regions, such as 102D. In other examples, one or more other subcutaneous or external locations can accommodate the wireless energy transmission source and inductive antenna 108, including, for example, the vena cava, pericardial space, or esophageal space. FIG. 10 shows an example of an external wireless energy transmission source 1040.

In certain examples, control of initiation, timing, or delivery of electrostimulation is provided by the CRM device 120 comprising one or more sensing electrodes 122A, 122B disposed on the housing 126B or header 126A of the CRM device 120. The sensing electrodes 122A, 122B can, among other things, provide electrogram sensing of intrinsic cardiac activity, evoked response to electrostimulation, or parameters related to patient activity level (e.g., respiration, heart rate). Additionally, in another example, one or more fixation devices 105, 107 can provide one or more sensing electrodes, and conductively couple one or more sensed signals via leads 104, 106 to the CRM device 120.

In some examples, delivery of multiple seeds can allow defibrillation or cardioversion to be achieved using electrostimulation by the seeds, while decreasing, minimizing, or eliminating pain or patient discomfort. To achieve effective cardioversion or defibrillation, multiple re-entrancy paths within the cardiac tissue can be broken, or de-sensitized. The total delivered energy used to de-sensitize (e.g., inhibit activation of) enough myocardium, 102E, for instance, can be substantially larger if only a single defibrillation vector is used (e.g., a single pair of electrodes), compared to using multiple defibrillation sites.

Figure 2:
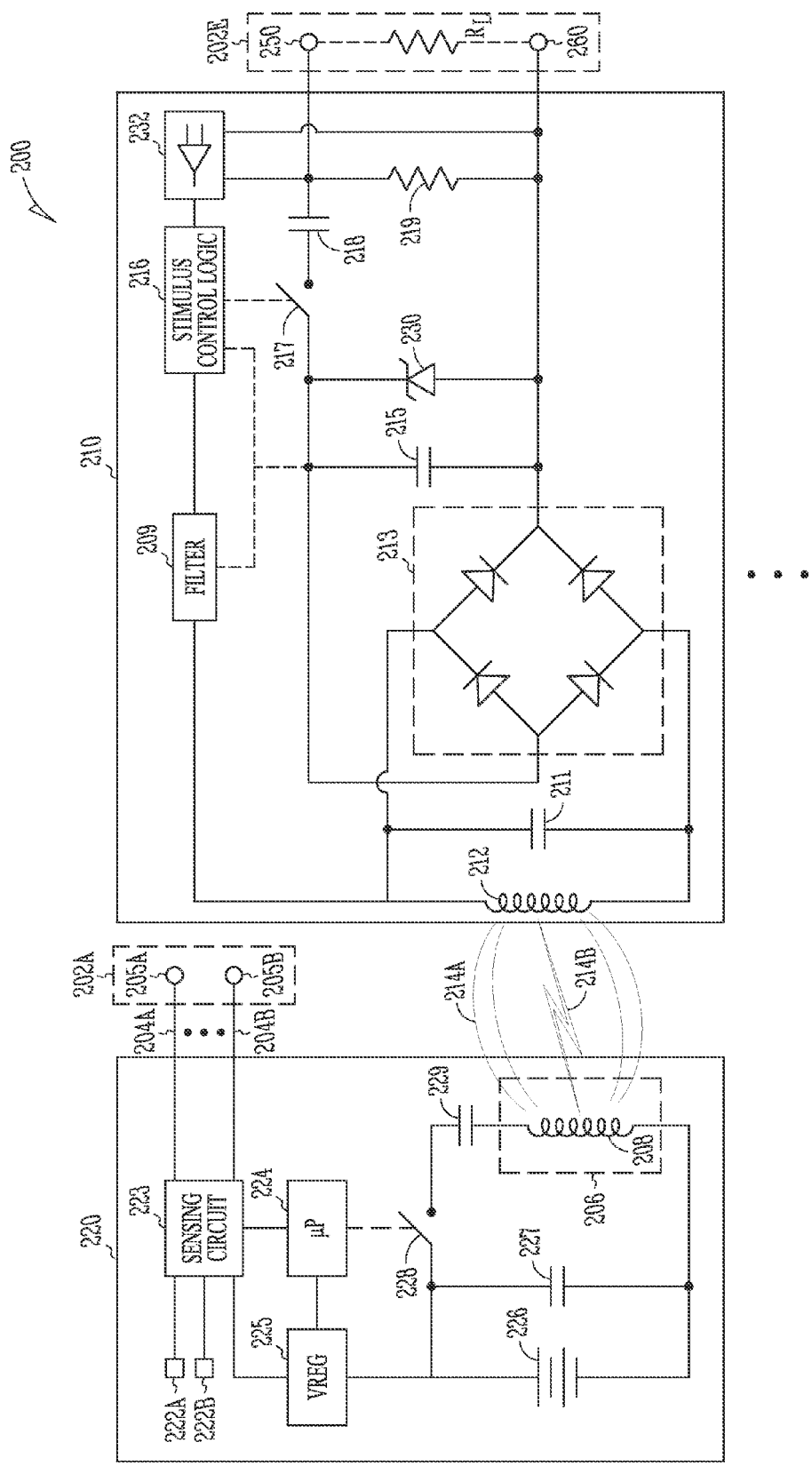
FIG. 2 is a schematic diagram illustrating generally an example of at least a portion of a wireless electrostimulation system including a wireless energy transmission source and a wireless electrostimulation node.

FIG. 2 is a schematic diagram illustrating generally an example of at least a portion of a wireless electrostimulation system 200 including a wireless energy transmission source 220 and a wireless electrostimulation node (seed) 210.

The example in FIG. 2 shows a wireless energy source 220 that can include a battery 226, voltage regulator 225, and a microprocessor 224. In certain examples, the microprocessor 224 comprises input-output (I/O) capability such that a switching structure 228 can be coupled to the microprocessor 224 to control current flow from the battery 226 or an optional transient energy storage device such as a capacitor 227 to an inductive antenna 206. In one example, the inductive antenna is comprised of a wire loop 208. In another example, the inductive antenna 206 comprises of multiple wire loops 208 that can be configured spatially orthogonal to one another such as to reduce orientation sensitivity. A tuning element 229 can be used to allow a range of frequencies to be selected at which a time-varying magnetic flux 214 will be generated by the inductive antenna 206. The resulting inductance-capacitance (LC) circuit forms a resonant "tank" circuit, which can have an operable range of resonant frequencies selected from a range of 300 KHz to 10 MHz, but selected below the self-resonant frequency of the inductor 208 comprising the inductive antenna 206.

Some examples of the tuning element 229 can include, but are not restricted to, a capacitor, a variable-capacitance diode ("varicap" diode), an active circuit modeling a capacitor of a selected value, etc. In some examples, the switch 228 and tuning element 229 can be replaced, such as by a combination of a voltage-controlled oscillator and power amplifier coupled to directly drive the inductive antenna 206 such as to achieve generation of magnetic flux 214 at a specified range of frequencies. The switch 228 can be realized either mechanically as a microminiature relay device, or as solid-state device (e.g., FET, BJT, IGBT, SCR, or other thyristor). In some examples, the regulator 225, microprocessor 224, sensing circuit 223, and switching device 228 are co-integrated in a single integrated circuit or multi-chip module package. Note that the term "microprocessor" can also include, among other things, a microcontroller device including one or more of volatile or non-volatile memory, multiple input/output channels, analog-to-digital conversion devices, power supplies, or digital-to-analog conversion devices that can be co-integrated in, for example, a single integrated circuit, single circuit package, multi-chip module package, hybrid, polyimide flex-circuit assembly, etc.

In some examples, the initiation, timing, duration and frequency range of the generation of magnetic flux 214 is controlled by the microprocessor 224 wherein the microprocessor 224 is provided with input from a sensing circuit 223. The sensing circuit 223 can be coupled to, for example, wire leads 204A, 204B implanted subcutaneously within cardiac tissue 202A. In another example, the wireless energy transmission source can be external to the body, and leads 204A, 204B can be coupled to the skin of the patient (e.g., to measure electrocardiograms). In the example shown in FIG. 1, the transmission source 220 can comprise one or more sense electrodes 222A, 222B coupled to the sensing circuit. In one example, sense electrodes 222A, 222B are disposed on the housing of wireless energy transmission source 220.

The time-varying magnetic flux 214 may be generated for either transferring operating energy 214A to the seed device 210, or for communication 214B with the seed device 210 (e.g., one range of frequencies can be established for wireless energy transfer, and a second range of frequencies can be established for commanding the seed device 210 to deliver stimulus).

In the example shown in FIG. 2 filter 209 can discriminate between power 214A and communication 214B signaling. For example, filter 209 can be configured to detect a particular range of frequencies of time-varying flux 214B captured by the seed 210 such as by using an inductive pickup 212. The filter 209 can be coupled to stimulus control logic 216. Logic 216 can be configured to either inhibit or to initiate tissue electrostimulation, such as in response to the filter 209 detecting a specified signal. Filter 209 can include, in certain examples, a band-pass filter, which can be coupled to a threshold comparator. In certain examples, the filter 209 can include a digital demodulator. In some examples, communication signal 214B can be encoded digitally and transmitted concurrently to, or comprising, power signal 214A. Examples of digital encoding of communication signal 214B can include, but are not restricted to, on-off keying, amplitude-shift keying, phase-shift keying, frequency-shift keying, or the like.

In some examples, the combination of the capacitance of the tuning element 229 and actual or parasitic capacitances of the inductive antenna 206 can vary when the wireless energy transmission source is implanted in or near tissue 202E. The effect of tissue interaction with the system can be reduced by at least partially surrounding the inductive antenna 206 or inductive pickup 212 (see, e.g., FIG. 7) with a protective material or encapsulant. Such encapsulation can inhibit or prevent tissue 202E or liquid penetrating into the cavities between individual turns of a multi-turn inductive pickup 212 or inductive antenna 206, which would otherwise increase the effective relative dielectric constant seen by the pickup 212, or antenna 206.

In some examples, the microprocessor 224 can be configured to adjust the capacitance of the tuning element 229, or to adjust the frequency of a corresponding voltage-controlled oscillator, such as to achieve a desired level of efficiency in coupling to the implanted seed 210. In an example, cardiac pacing electrostimulus can be applied using electrodes 250 and 260, and the evoked response can be observed using either sensing electrodes 205A, 205B, 222A, 222B or an external electrocardiogram sensing apparatus. Tuning element 229, or a corresponding frequency synthesizer, can be adjusted by microprocessor 224, such as to vary the range of frequencies of magnetic flux 214 that are generated, for example, until a desired or reliable "capture." (e.g., activation of cardiac tissue resulting from electrostimulation) is observed.

The seed device 210 can include an inductive pickup 212 and an optional discrete tuning element 211. In an example, the value of the capacitance of element 211 can be selected before implant of the seed device, such as to achieve a desired resonant frequency when implanted, such as surrounded by blood or muscle tissue. In some examples, to reduce the size of the seed device 210, a discrete capacitor 211 can be omitted, and the capacitance used to achieve resonance of the inductive pickup 212 can be the parasitic capacitance of the physical coil structure of the inductive pickup 212 (for example, the inter-winding capacitance).

Inductively-coupled energy 214A can be rectified, such as by a full-wave rectifier 213, as shown in the example in FIG. 2, or by a half-wave rectifier, which can save space by reducing the number of diode components used in the seed device 210. Rectified energy can be stored in an optional energy storage device 215, such as shown in the example in FIG. 2. In an example, the energy storage device 215 can act like a filter capacitor, such as to help suppress ripple voltage. Stimulus control logic 216 can be coupled to a switch device 217. The switch 217 can include a solid-state device (e.g., FET, BJT, IGBT, SCR, thyristor, etc.). In an example, such as to reduce the size of the seed 210, the filter 209, logic 216, switch 217, and rectifier 213 can be co-integrated into a single integrated circuit package, or for example, into a multi-chip module, etc. similar to that described above in the context of the wireless energy source 220.

In some examples, multiple storage devices 215 and switches 217 can be used, such as to arrange stored voltages in a desired series, parallel, or series-parallel combination, such as to achieve an electrostimulus peak voltage in excess of the maximum voltage stored on a single storage device 215 using the power signal 214A.

A direct-current (DC) blocking device 218 can be used to inhibit a DC-stimulus component from being coupled to electrostimulus electrodes 250, 260. Electrostimulus electrodes 250, 260 can be conductively coupled to the muscle tissue 202E to be electrostimulated (e.g., myocardial tissue). In an example, electrode 250 can be used as the cathode electrostimulation electrode, and electrode 260 can be used as the anode electrostimulation electrode.

The blocking device 218 and the shunt device 219 can form a high-pass network configured such that the upper cutoff frequency and resulting time-domain pulse shape can be selected or even programmably adjusted such as to form a desired electrostimulus waveform. In an illustrative example, blocking device 218 can be selected as a capacitor having a capacitance of about 1 microFarad, and shunt device 219 can be selected as an approximately 5 kiloOhm resistor to achieve a desired cardiac tissue electrostimulation pacing pulse.

The present inventor has recognized that, among other things, tissue and body fluid inductive energy absorption and dispersive effects can rapidly increase at frequencies greater than 100 KHz. These effects can severely limit the range and maximum achievable efficiency of typical magnetic coupling schemes. One technique for decreasing the losses induced by such effects can be to substantially or completely surround the inductors 208, 212 with a high relative permeability magnetic material such as an iron-powder core or a ferrite material or the like. Such materials can magnify the magnetic flux density seen by wound structures nearby them, at a given incident magnetic field intensity.

The high relative magnetic permeability of such materials can render the resultant implantable device assemblies incompatible with magnetic resonance imaging (MRI) equipment. Forces or torques induced locally (e.g., induced in single components) associated with the strong bias field present near operating MRI equipment could result in mechanical damage to the inductive antenna 206 or inductive pickup 212 assemblies if they incorporate a high relative magnetic permeability material.

Additionally, operating MRI equipment can induce large voltages across the terminals of the inductive antenna 206 or inductive pickup 212, and large currents inducing an internal temperature rise. These effects can result in irreversible damage (e.g., electrical short-circuiting or dielectric failure) to the inductors 208, 212 or to other components electrically coupled to the inductors 208, 212, and possibly thermal damage to surrounding tissue 202E.

Additional protection devices (e.g., discharge tubes, gaps, solid-state transient-suppression devices) can be included to inhibit or prevent MRI-related electrical damage. In the case of the seed device 210, small size is generally desired (e.g., to allow intravascular introduction and placement) and such additional protection devices can take up additional space and could fail to mitigate the MRI-induced forces and torques.

The present inventor has also recognized, among other things, that ferrite core materials can also have limitations. For example, internal loss mechanisms can preclude their usage as core materials for highly-tuned inductors at frequencies in excess of a few MHz. This prevents the resonant "tank circuits" in the inductive transmit network, 229, 208 and inductive receiver network 212, 211, from achieving high power coupling efficiencies, since the Quality factors ("Q") of both networks are limited by the resistive damping effects of increasing losses within the ferrite core material.

By contrast, the present inventor has recognized that, in a different approach, the core materials or mechanical supports surrounding the inductive antenna 206 or inductive pickup 212 can be selected to have a relative magnetic permeability less than 1.1, and can be comprised of one or more materials other than ferrites, or the core material or mechanical support can provide the antenna 206 or the pickup 212 with an effective relative magnetic permeability substantially equal to 1 (such as by using a non-magnetic material, such as air, blood, bodily tissue, bodily fluid, or one or more other materials for the core material or the mechanical supports).

Materials, such as shape-memory Nickel-Titanium (NiTi or Nitinol) compounds, are effectively non-ferromagnetic and can have other beneficial mechanical properties. For example, the shape-memory property can be used to expand (e.g., after implant) a loop antenna 206 or inductive pickup 212. By increasing or maximizing the area of a loop forming an inductive antenna 206, or inductive pickup 212, the mutual coupling of two such inductive devices in proximity can be enhanced. Such materials can also help mitigate ferrite efficiency loss and allow more efficient coupling of time-varying magnetic flux through tissue, such as at frequencies up to several MHz. The term "air core" can be used to describe the inductive transmitter 208 and receiver 212 structures, even though the actual construction of such devices might include non-ferromagnetic metallic support structures and, when implanted, tissue or bodily fluid may be present within the core of the inductive transmitter 208 or receiver 212.

A mathematical analysis of a simplified combination of the wireless energy source 220 and seed 210 allows power coupling efficiency, η, and electrostimulus output voltage magnitude, $|V_L|$, to be computed. The combination of switch 228, and battery 226 can be represented as an AC voltage source operating at angular frequency ω, and peak output voltage $V_0$. The inductive antenna 206 can be modeled as a combination of an ideal inductor 208, as L, in series with a transmit circuit resistance R. Tuning element 229 can be modeled as a capacitor, C. The transmit circuit impedance can be represented as $Z=R+i(\omega L-1/\omega C)$, in which $i=\sqrt{-1}$. At resonance, $C=1/\omega^2 L$, and $Z=R$. The imaginary components, due to the reactances of the capacitor and inductor, can cancel each other (unity power factor).

Similarly, for the circuitry included in seed 210, the inductor 212 can be modeled as $L_1$, and its corresponding loss as resistance "r" in series with $L_1$. Tuning element 211 can be modeled as a parallel capacitor $C_1$, and the tissue load 202E appearing across electrostimulus electrodes 250, 260 can be modeled as $R_L$. Neglecting the rectifier 213, switch 217, shunt capacitor 215, blocking device 218, and shunt resistor 219, the receiver inductive pickup impedance can be represented as $Z_1=r+i\omega L_1$ and the impedance associated with the tissue load and tuning element can be represented as $Z_L=R_L/(1+i\omega R_L C_1)$.

For the seed 210, this corresponds to a lossy inductive pickup $Z_1=r+i\omega L_1$ in parallel with a load comprised of $Z_L=R_L/(1+i\omega R_L C_1)$. The total parallel impedance $Z_2=r+R_L/(1+(\omega R_L C_1)^2)+i[\omega L_1-\omega R_L^2 C_1/(1+(\omega R_L C_1)^2)]$. At resonance, $1+(\omega R_L C_1)^2=R_L^2 C_1/L_1$, and $Z_2=r+R_L/(1+(\omega R_L C_1)^2)=r[1+L_1/(rR_L C_1)]$. The magnitude of $Z_L=\sqrt{(L_1/C_1)}$.

The mutual inductance, M, of transmit antenna 206 and inductive pickup 212 can be represented as the product of the self inductances of the two inductors 208, 212 and a coupling constant, κ: $M^2=\kappa L L_1$. Power coupling efficiency and peak output voltage at the tissue load 202E can be represented as:

$$\eta = \kappa Q Q_1 x/[(1+x)(1+x+\kappa Q Q_1)] \quad (1)$$

$$|V_L| = \sqrt{(R_L/R)\kappa Q Q_1 x} V_0/(1+x+\kappa Q Q_1) \quad (2)$$

where $Q=\omega L/R$=quality factor of transmitter, $Q_1=\omega L_1/r$=quality factor of receiver, and $x=L_1/(rR_L C_1)$. The following relation can be obtained:

$$\kappa Q Q_1 \gg 1+x, \eta \rightarrow x/(1+x) \quad (3)$$

and when $x \gg 1$, the power coupling efficiency, η, approaches 1 (corresponding to 100%). Thus, for small values of the coupling constant, κ, if the quality factors are sufficiently large, the power coupling efficiency can approach unity.

Generally, the seed 210 receiver resonant frequency and quality factor $Q_1$ can vary depending on the specific implant configuration of the inductive pickup 212, and the resulting tissue and blood proximity effects on the electrical response of the inductive pickup 212. However, by actively statically or dynamically varying the value of tuning element 229 in the wireless energy source 220, as described previously, the wireless energy source 220 transmitter resonant frequency can be varied, such as to compensate for changes in the seed 210 receiver resonant frequency or to control electrostimulus amplitude or energy achieved at electrodes 250, 260.

If the transmitter 220 quality factor, Q, is selected to be much greater than the receiver quality factor, $Q_1$, the receiver can have a broader "tuning envelope" than the transmitter. With a broader seed 210 receiver response characteristic, the transmitter tuning element 229 can be adjusted more easily (e.g., less precisely) to provide an operating frequency at resonance corresponding the to resonant frequency of the receiver in seed 210 (e.g., the transmitter can be tuned to be more sharply "peaked" at resonance than the receiver, and transmitter resonant frequency can then be swept until centered on receiver resonant frequency).

In some examples, varying the resonant frequency of the transmitter by changing the capacitance of tuning element 229 can also control the magnitude of the electrostimulus voltage coupled to the tissue load 202E. Selecting a value for tuning element 229 that shifts the resonant frequency of the wireless energy source 220 away from the resonant frequency of the seed 210 can result in decreasing maximum voltage, $|V_L|$, coupled to the tissue load 202E. This can reduce the size of the seed 210 by eliminating or reducing the complexity of logic 216 and the switch device 217 such as by allowing electrostimulation amplitude control to be accomplished by the wireless transmission source 220.

In some examples, power signal 214A can be limited in duration or maximum amplitude such as to avoid tissue heating or regulatory limits for average or instantaneous power transmitted through tissue. The resulting rectified energy can be integrated or otherwise accumulated by, for example, storage device 215. $|V_L|$ can, for instance, be established by a series- or shunt-regulation component such as a Zener diode 230.

In some examples, Zener diode 230 can be used to simplify or eliminate stimulus control logic 216 and switch device 217 when a pulse-width modulation (PWM) scheme is used at the transmission source 220. A microprocessor, state machine, timing logic, and the like can be omitted from the seed 210 to reduce complexity, physical volume, etc.

In one example, stimulus control logic 216 can still be used to inhibit electrostimulation delivery to tissue load 202E (e.g., by opening switch device 217 when an intrinsic event is sensed), but is not required to control the level of electrostimulation energy content delivered to tissue load 202E.

In some examples, power signal 214A can be established at a specific burst duration (e.g., a burst can be a square pulse envelope commencing a sequence of multiple resonant oscillations). The duration or pulse width of the burst of power signal 214A can be related to the energy content delivered to the tissue load 202E when the regulation device 230 is clamping the voltage across the storage device 215.

If tissue 202E is modeled as a cardiac tissue load having a resistance $R_L$=1 kiloOhm in parallel with a series-combination of a 1 kiloOhm resistor ($r_L$) and a 1 microFarad capacitor ($C_L$), a cardiac tissue electrostimulation pacing pulse of greater than 4V peak amplitude, $|V_L|$, can be achieved using a resonant frequency of 1 MHz.

For the leading edge of an example of a cardiac tissue electrostimulation pulse, the load capacitor can be represented effectively as a short circuit, and the AC resistance of the model cardiac tissue load 202E is equal to around 500 ohms (1 kiloOhm in parallel with 1 kiloOhm).

In some examples, the burst duration of power signal 214A can be controlled by the microprocessor 224 and switching element 228 at the transmission source 220 to achieve a desired energy content coupled to the tissue load 202E.

A theoretical voltage delivered across a cardiac tissue capacitance, $V_{CAP}$, can be represented as:

$$V_{CAP} = V_{CLAMP}[1 - e^{-w/r_L C_L}] \quad (4)$$

where $V_{CLAMP}$ represents the voltage clamping threshold of the regulating device 230, and w represents the burst pulse duration (in seconds). For small burst pulse durations, $V_{CAP}$ can be approximated as:

$$V_{CAP} = V_{CLAMP}[w/r_L C_L] \text{ for } w << r_L C_L \quad (5)$$

In an example, $V_{CLAMP}$ can be 5.6V (e.g., established by a Zener diode 230), w can be 775 microseconds, $r_L=R=1$ kiloOhm, and C=1 microFarad. Using EQUATION 4, $V_{CAP}$ can be computed as approximately 3 Volts. In another example, w can be 1250 microseconds, and $V_{CAP}$ can be computed as approximately 4 Volts.

In some examples, the volume occupied by seed 210 can be decreased by limiting the total energy stored, for example, storage device 215. An estimate of the desired stored energy for various electrostimulation pulses can be made. For example, if $R_L=500$ Ohms, and $|V_L|=2.5V$, a square-wave pulse of duration T=0.4 milliseconds can correspond to a stored electrostimulation energy of $T|V_L|^2/R_L=5$ microJoules.

Storage device 215 can be specified as a capacitor=$C_S$, in microFarads. The energy stored in capacitor 215 can be represented as $\frac{1}{2}C_S|V_L|^2$. The number of electrostimulation delivery cycles that the energy stored in the capacitor 215 can deliver can be represented as: the energy stored on the capacitor=$\frac{1}{2}C_S|V_L|^2$, divided by the electrostimulation energy consumed by a single electrostimulation cycle delivered to the tissue impedance=$T|V_L|^2/R_L$. Thus, the number of cycles that capacitor 215 can supply can be represented as $=R_L C_S/2T$.

Tradeoffs can be made between storage device 215 value $C_S$, load resistance $R_L$ and, for example, pulse width, to achieve a desired seed 210 volume and a desired electrostimulation duration, for instance, during an interval when inductive power signal 214A can be inhibited.

For example, the number of desired electrostimulation cycles can be =N, and the capacitor value for storage device 215 to provide N electrostimulation cycles can be represented as $C_S=2TN/R_L$. In an example, an electrostimulation pulse duration can be specified as T=0.4 msec, the load resistance can be $R_L=500$ Ohms, and the capacitance $C_S$ can be represented for N=1 as $C_S=1.6$ μF. A low voltage 1.6 μF capacitor 215 can be small (e.g., sub-millimeter dimensions on each axis).

In some examples, back-up storage can be desired for patient protection (e.g., to provide continued electrostimulation for a limited duration in the temporary absence of power signal 214A). A heart rate can be specified=$H_R$ in Hertz, a number of cardiac cycle to be paced in a total time=$T_{stored}$, in seconds, can be represented=$H_R T_{stored}$, and the size of the capacitor to store a corresponding amount of energy can be represented, $C_S=2TH_R T_{stored}/R_L$. For example, one hour=3600 sec of stored electrostimulation energy and a heart rate of 72 beats per minute or 1.2 Hz can be specified, resulting in, for example, a number of pacing electrostimulation cycles $H_R T_{stored}=4320$, and a total stored energy=21.6 milliJoules. The tissue impedance $R_L$ can be specified as 500 Ohms and pulse width can be specified as T=0.4 msec, and the capacitance 215 can be represented $C_S=6912$ μF. Such a capacitor can occupy several cubic millimeters of volume in the receiver circuit.

In some examples, a compromise between capacitor 215 value Cs and the physical size of the capacitor 215 can be made. For example, a capacitor 215 can be specified, $C_S=320$ μF, and electrostimulation pulses can be specified, $|V_L|=2.5$ volts.

In an example, the total energy stored on capacitor 215 is 1 milliJoule, and can be enough energy to deliver 200 electrostimulation cycles of pulse width T=0.4 msec to into a tissue load $R_L=500$ Ohms. In an example, capacitor 215 can be specified $C_S=320$ μF and the electrostimulation cycle rate of 72 electrostimulation cycles per minute can result in continued electrostimulation delivery, for approximately 2.8 minutes, by seed 210, after energy 214A input to $C_S$ is inhibited.

Capacitor 215 can also be specified to accommodate the quiescent power consumed by, for example, stimulus control logic 216 comprising a microprocessor, which can be very small depending upon the device used, but in some cases can be comparable to, or larger than, the average pacing power. In some examples, the power consumed by the receiver circuit 210 can be reduced if stimulus control logic 216 and filter 209 are omitted and switch 217 is permanently closed or omitted. For some examples, the capacitor Cs can be a filter capacitor, and the energy 214A received by the seed 210 is rectified and delivered directly to the tissue load (e.g., the delivered electrostimulation pulse width can correspond to the width of a transmitted energy 214A burst pulse, provided that the time constant $\tau=C_S R_L$ is less than about one half of the pulse width). In some examples, direct conversion of energy 214A into an electrostimulation delivery can be achieved and $C_S<0.4$ μF can be specified (e.g., corresponding to an electrostimulation pulse width of T=0.4 msec and load $R_L=500$ Ohms).

In some examples, sensing circuitry 232 can be coupled to cardiac tissue 202E to provide signaling to stimulus control logic 216 in response to sensed potentials detected by the sensing circuitry 232. Signaling to stimulus control logic 216 can occur in response to intrinsic tissue activity (e.g., sensing circuitry 232 establishes a threshold level or window and intrinsic activity can cause a voltage fluctuation exceeding a threshold level or window). Stimulus control logic 216 can inhibit electrostimulation using switch 217 in response to, for example, detection of sensed events provided by sensing circuitry 232.

In some examples, a shunt device 219 can also provide charge neutralization. Charge neutralization can include providing a path between the electrostimulus electrodes 250, 260 to slowly discharge an afterpotential occurring during or after an electrostimulation, resulting in a net neutral charge delivered by the electrostimulation electrodes 250, 260. For the example of a pacing waveform described above, charge neutralization can be observed as a smaller amplitude negative-phase pulse of longer duration following the positive-phase cardiac tissue electrostimulation pulse.

Figure 3A:
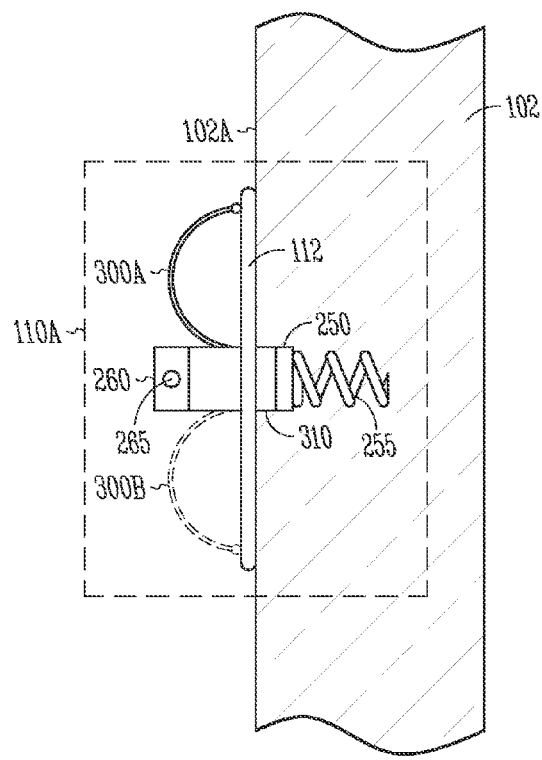
FIGS. 3A-B are views illustrating generally at least a portion of an example of a wireless electrostimulation node included in a wireless electrostimulation system.
Figure 3B:
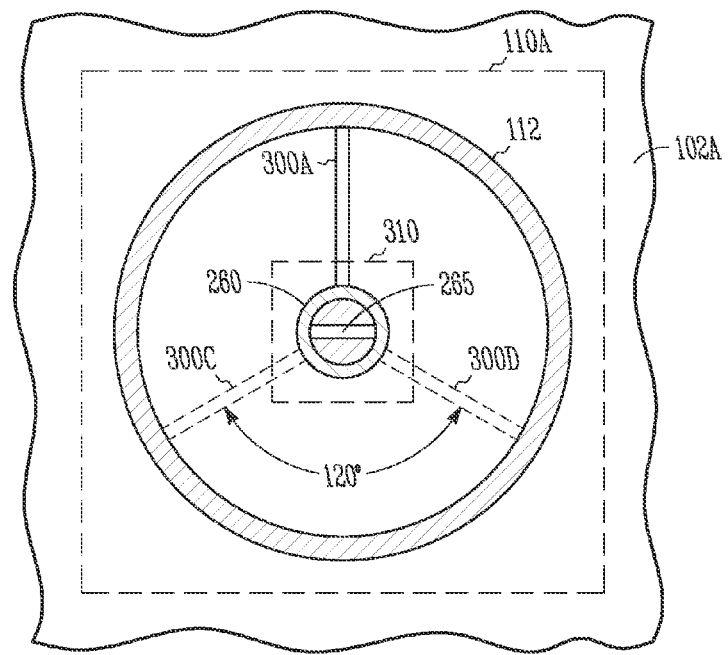
Figure 7:
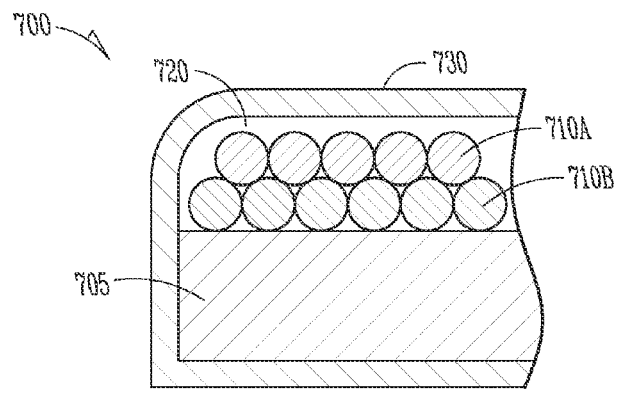
FIG. 7 is a partial cross-sectional view illustrating generally an example of at least a portion of a wireless electrostimulation system including a wire loop and a mechanical support, showing a local encapsulant surrounding the wire loop and a bulk encapsulant surrounding both the mechanical support and wire loop.

FIGS. 3A-B are views illustrating generally at least a portion of an example of a wireless electrostimulation node 110A or "seed" that can be included in a wireless electrostimulation system. Wireless electrostimulation node 110A can be configured as a cardiovascular wireless electrostimulation node fixed to or in myocardial tissue 102. Inductive energy can be coupled to an inductive pickup 112 supported by one or more shape-memory or other mechanical struts 300A, 300B, 300C, 300D. In an example, as shown in FIG. 3B, the struts 300A, 300C, 300D can be disposed radially around the cylindrical housing 310 such as at angles of 120 degrees with respect to each other. FIG. 7 shows an example of a partial cross section view of the inductive pickup 112 comprising both a mechanical support and a separate inductive wire loop, attached to the mechanical support. In another example, the inductive pickup wire loop itself can serve as both the electrical pickup and mechanical support, reducing the complexity of the assembly.

In some examples, a tissue attachment mechanism such as helical fixation device 255 can secure a cylindrical housing 310 to myocardial tissue 102. This can pull the cylindrical housing 310 to a desired depth within myocardial tissue 102 such as with an objective of leaving as little of the housing 310 protruding out of the myocardial tissue 102 as possible. This can reduce or minimize the possibility of impingement against other tissue such as during a heart contraction. The total length of the seed 110A can be selected to reduce or minimize the likelihood of penetrating the far side of the myocardium 102.

In an example, assuming a nominal minimum myocardial wall thickness of 10 mm, the cylindrical housing 310 can be configured to have a diameter of less than or equal to 2 mm, and a length of less than or equal to 5 mm, such that a total length of the cylindrical housing 310 plus the anode 260, cathode 250, and fixation device 255 is less than 10 mm, which is short enough to avoid piercing the far side of the myocardium. In some examples, discrete internal electronic components can be included in the cylindrical housing 310. Housing 310 internal electronic components can be selected for reduced size, and can include, among other things, one or more discrete surface-mount capacitors, discrete surface-mount resistors, or discrete surface-mount diodes, and the like. In an example, a single diode can be used as a half-wave rectifier to reduce housing 310 volume.

A cathode electrode 250 can provide a first electrostimulation electrode that can be embedded into myocardial tissue 102. In certain examples, all or a portion of fixation device 255 can be conductively coupled to electrode 250 such as to target electrostimulation to a specific depth of myocardial tissue 102. An anode electrode 260 can provide a second electrostimulation electrode that can be in contact with either other cardiac tissue 102 or blood, for instance to provide a return path to complete the electrostimulation circuit.

For example, in an endocardial application, the cardiovascular wireless electrostimulation node 110A is configured for intravascular delivery to the interior of the heart, via one or more blood vessels, such as transluminally through a lumen of a catheter, and can be embedded in myocardium 102 penetrating an endocardial wall 102A such as the left ventricular free wall. Blood in contact with anode 260 can provide a conductive path for electrostimulation energy allowing contractile electrostimulation (e.g., pacing) of the myocardium 102 coupled to cathode 250.

In some examples, a retainer shaft 265 can be included, such as to allow for manipulation of the seed 110A during implantation (for instance, to secure an actuator assembly to the seed 110A as part of an intravascular delivery system).

Struts 300A-D can be constructed from a spring-like (e.g., self-expanding or self-opening) flexible shape-memory material such as a NiTi (Nitinol) compound, such as to accommodate a desired insertion depth of the cylindrical housing while flexibly maintaining an approximately circular loop shape for inductive pickup 112. In some examples, struts 300A-D can be welded or adhered to an inductive pickup 112 comprising a mechanical support made of a shape-memory material such as a NiTi (Nitinol) compound.

Figure 4A:
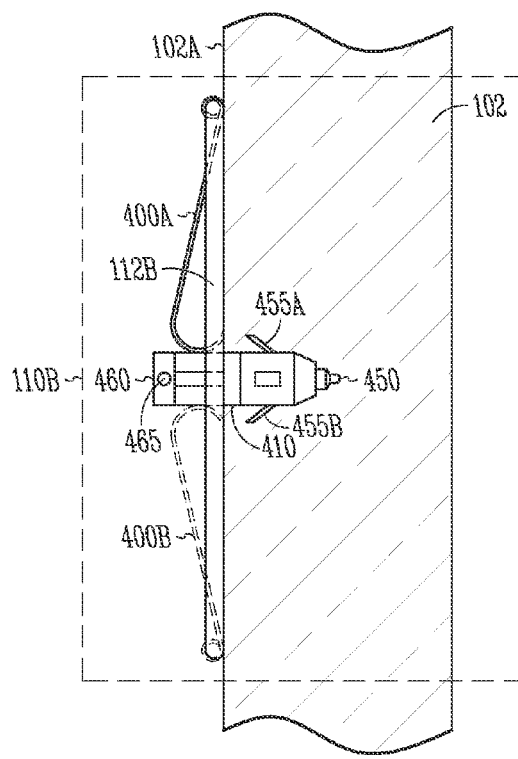
FIGS. 4A-B are similar to FIGS. 3A-B, but illustrate generally at least a portion of another example of a wireless electrostimulation node included in a wireless electrostimulation system.
Figure 4B:
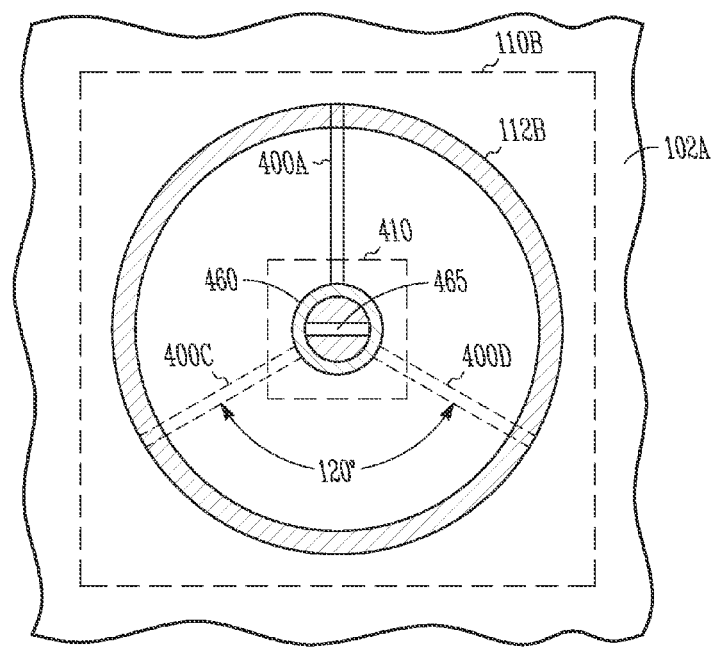

FIGS. 4A-B are similar to FIGS. 3A-B, but illustrate generally at least a portion of another example of a wireless electrostimulation node 110B that can be included in a wireless electrostimulation system. The combination of one or more struts 400A-D or barb structures 455A-B can provide fixation of the seed 110B in, for example, cardiac tissue 102. In these examples, rotation is not required in order to establish a specified depth of penetration in myocardium 102. Housing 410 can be pushed into tissue 102 to a desired depth, such as to avoid piercing an epicardial wall opposite penetration into the myocardium 102. In the example in FIGS. 4A-B, the housing 410 is shown as cylindrical, but the actual cross-section of the housing can also be configured as a polygon such as to inhibit or to prevent rotation within an implant delivery catheter.

Implant depth can be controlled or limited such as by modifying strut structures 400A-D to provide a "J"-shaped loop or hook extending outwards from housing 410 as shown in the example of FIG. 4A. As the seed 110B further penetrates myocardium 102, eventually struts 400A-D can limit further insertion (e.g., insertion force increases substantially as "J"-shaped loops impact heart wall 102A). Side barbs 455A-B can be included such as to inhibit or prevent removal of seed 110B without substantial force. In this manner, specified depth can be obtained or maintained. In some examples, barbs 455A-455B can be configured to expand outward or retract inward, such as during implantation, such as to facilitate one or more of implantation, removal or retraction of seed 110B.

A variety of different electrostimulus electrode shapes can be used, including, for example, a point-type cathode electrode 450 such as shown in FIG. 4A, and a corresponding anode electrode 460.

Struts 400A-D can be mechanically secured to inductive pickup 112B, such as by wrapping around or encircling the cross section of inductive pickup 112B, for example, such as shown in FIG. 4A. Other techniques of mechanically coupling struts 400A-D can include welding or adhering one or more of the struts 400A-D, such as to one or more of the housing 410, inductive pickup 112B, etc.

Generally, a retainer shaft 465 can be provided, such as to temporarily secure the seed 110B to an actuator component of an intravascular delivery system during implant.

In some examples, one or more elements of the seeds 110A and 110B shown in FIGS. 3A, 3B, 4A, 4B can be coated with an anti-coagulant or other treatment, such as to suppress clot or thrombus formation. In some examples, one or more elements of the seeds 110A, 110B can be finished with a surface treatment, such as to enhance tissue ingrowth. In some examples, the seed 110A, 110B can be incorporated into the tissue 102. Such embedding can reduce the likelihood of thrombo-embolism, and can also reduce the threshold energy that achieves desired electrostimulation (e.g., reduction of myocardial pacing threshold voltage).

Examples of tissue ingrowth enhancing treatments include surface roughening or texturing, or one or more other porosity-enhancement treatments. Examples of elements that can be treated with a tissue ingrowth enhancing surface finish include the strut structure(s) 300A-D, 400A-D, the inductive pickup 112A or 112B, cylindrical housing 310 or 410, etc.

In certain examples, one or more elements of the seeds 110A and 110B can include one or more materials that can be selected for radio-opacity, such as to enhance visibility of an implanted component during radiographic medical imaging.

Figure 5:
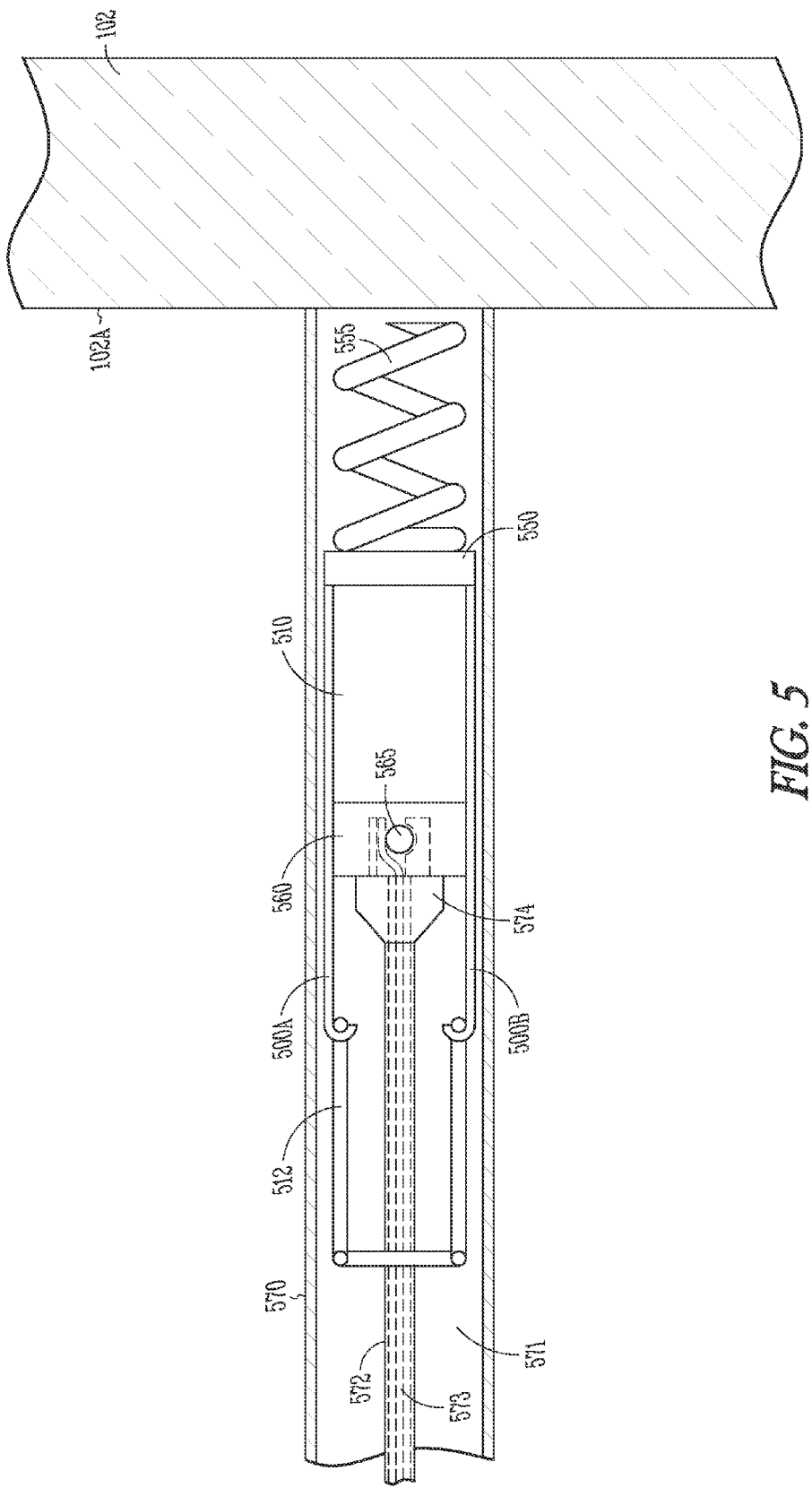
FIG. 5 is a partial cross-sectional view illustrating generally an example of at least a portion of a wireless electrostimulation system including a delivery catheter containing a wireless electrostimulation node.

FIG. 5 is a partial cross-sectional view illustrating generally an example of at least a portion of a wireless electrostimulation system including an elongate intravascular delivery catheter 570, such as for carrying or passing a wireless electrostimulation node housing 510 through a lumen 571 formed by the catheter 570.

In some examples, venous access can be achieved via the subclavian vein or femoral artery, and a guide catheter can then be inserted. For example, once a guide catheter has achieved access to an endocardial region of the heart 102A, a delivery catheter 570, for example as shown in FIG. 5, can be passed transluminally through the lumen of the guide catheter. The delivery catheter 570 can be open at an end near a cardiac tissue target 102. The delivery catheter 570 can be large enough in hollow cross sectional area forming the lumen 571 to allow a cardiovascular wireless electrostimulation node housing 510, expandable inductive pickup 512 and one or more expandable struts 500A, 500B to be routed through one or more blood vessels via the catheter 571 and endocardially implanted entirely within the heart at the tissue target 102.

The rotational position and position along the length of the delivery catheter 570 of the seed housing 510 can be manipulated, in an example, such as by a hollow, flexible actuator 572. The actuator 572 can be mechanically coupled to a retainer pin 565 that can be connected to the seed housing 510. A fingered-adaptor 574 can be used to engage the retainer pin 565 and to displace it into a corresponding recess on the fingered-adaptor 574 such as by using a locking wire 573.

At the distal end of the delivery catheter, outside the body, a plunger or other similar manipulator can be used, such as to apply rotational or translational (e.g., sliding) force to actuator 572. For example, if a helical tine fixation device 555 is used, the actuator 572 can transmit rotational force to the seed housing 510 to screw the tine 555 into myocardial tissue 102, such as to achieve a desired depth during implantation of the seed housing 510.

During the implant procedure, one or more struts 500A, 500B can be used to couple the inductive pickup 512 to the mechanical housing 510 of the seed. The struts 500A, 500B can be delivered in folded or compressed form, such as to reduce cross-sectional area during delivery. In an example, such as shown in FIG. 5, the struts 500A, 500B and inductive pickup 512 can be folded linearly parallel to the body of the housing 510. In another example, to further reduce the net length of the entire assembly during implant, the struts 500A, 500B and inductive pickup 512 can be wound spirally around the housing 510. Once a desired depth of fixation device 555 is achieved, locking pull-wire 573 can be pulled. For example, if attached to an independent manipulator at the distal end of the delivery catheter 570, pull-wire 573 can be removed by pulling the manipulator. Once locking pull-wire 573 has been pulled clear of retainer pin 565, the entire delivery catheter 570 and actuator rod 572 can be pulled away from cardiac tissue wall 102A. This allows seed housing 510, and fixation 555 to remain.

Figure 6:
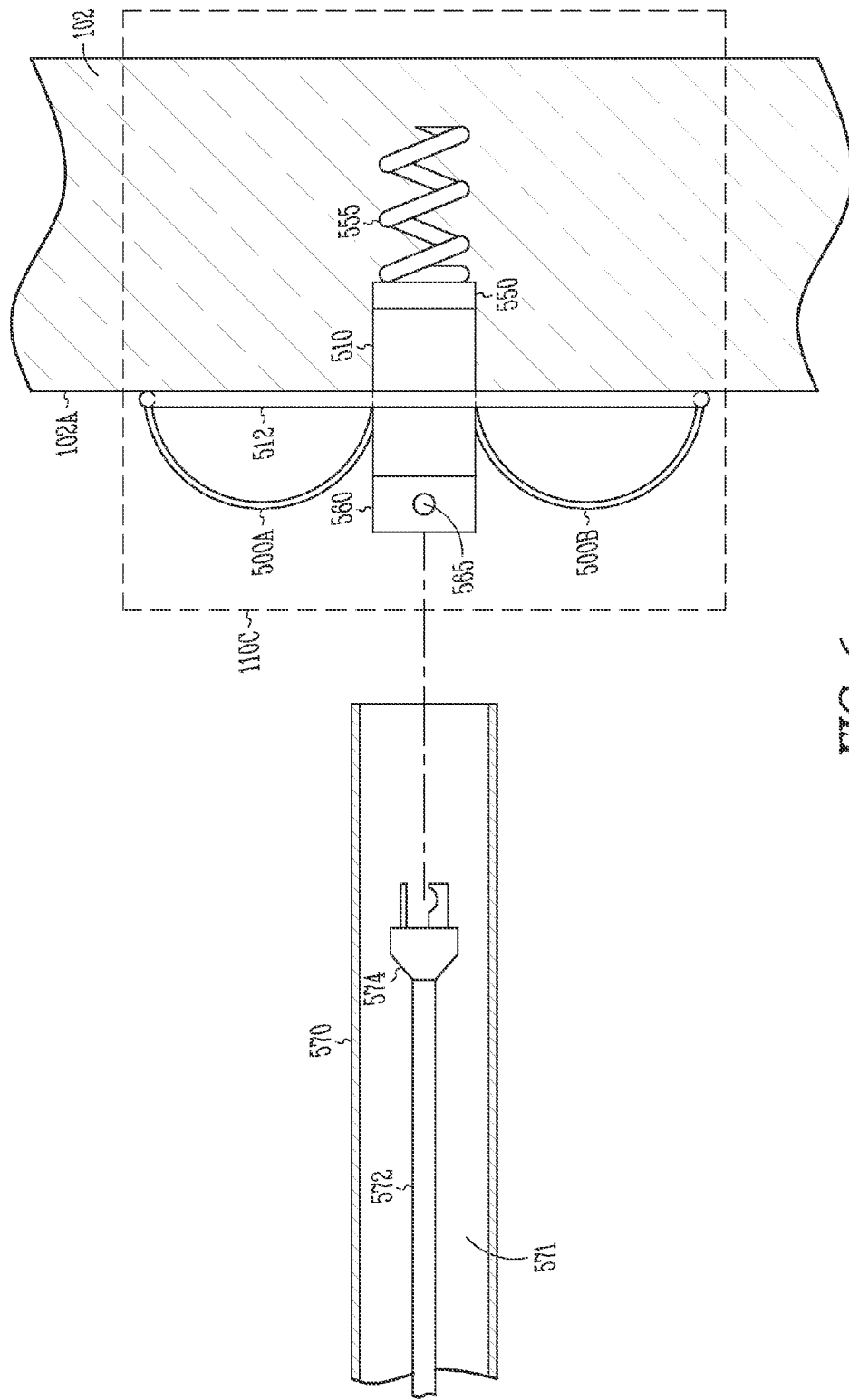
FIG. 6 is a partial cross-sectional view, similar to FIG. 5, but illustrating generally an example of at least a portion of a wireless electrostimulation system including the removal of a pull wire and the retraction of an actuator and delivery catheter.

FIG. 6 is a partial cross-sectional view, similar to FIG. 5, but illustrating generally an example of at least a portion of a wireless electrostimulation system including the removal of a pull-wire 573, the retraction of an actuator rod 572 and fingered-adaptor 574 through the hollow region, such as a lumen 571, of a delivery catheter 570, and the retraction of the catheter 570 from a cardiac tissue wall 102A. In this example, retainer pin 565 is no longer captive, thus seed assembly 110C remains at the cardiac tissue location 102A, 102.

In some examples, when delivery catheter 570 is pulled away from cardiac tissue wall 102A, inductive pickup 512 can expand to an outer diameter of, for instance, 2 centimeters. The size of the inductive pickup 512 when folded, as shown in FIG. 5, can be related to the size of the inductive pickup 512 when expanded, as shown in FIG. 6. The expanded outer diameter of inductive pickup 512 can be selected to allow for intravascular delivery using delivery catheter 570.

Once clear of the hollow region, such as the lumen 571, of the delivery catheter 570, shape-memory mechanical struts 500A, 500B can expand the inductive pickup 512, such as by using a self-expanding shape-memory material. In an example, additional expansion force and shape-memory can be provided by the inductive pickup 512 itself comprising a mechanical support that can be separate from the struts 500A-B. See FIGS. 7-9 for examples of inductive pickup and inductive antenna configurations.

Similar to FIGS. 3A-B, and FIGS. 4A-B, fixation device 555 can help retain the seed 110C, such as at a specified depth in myocardial tissue 102. Anode 550 and cathode 560 electrodes provide electrostimulus energy.

FIG. 7 is a partial cross-sectional view illustrating generally an example of at least a portion of a wireless electrostimulation system including an inductive assembly 700. In this example, the inductive assembly 700 includes windings of a wire loop 710A, 710B and a mechanical support 705. In this example, a local encapsulant 720 can be provided, such as for surrounding the wire loop windings 710A, 710B. A bulk encapsulant 730 can be provided, in certain examples, such as for surrounding both the mechanical support 705 and wire loop windings 710A, 710B. The cross-sectional view of the assembly 700 can describe either an inductive pickup included as a portion of a seed device (such as shown in FIG. 3A-B), or, for example, to an inductive antenna included as a portion of a wireless energy source (such as shown in FIG. 1).

In the example shown in FIG. 7, multiple windings 710A, 710B can be disposed adjacent to or near a mechanical support 705. The windings 710A, 710B can be constructed of flexible insulated wire. Individual windings 710A, 710B, can themselves be constructed of multiple strands of non-insulated wire, such as for providing enhanced flexibility. In an example, Litz wire (e.g., comprising multiple strands of silver wire) can be selected, such as for providing flexibility and improved magnetic performance, such as discussed below with respect to the example of FIG. 12. In another example, insulated silver wire can be used for one or more of the wire loops 710A, 710B.

In the example shown, encapsulant 720 can serve to inhibit or prevent blood or moisture ingress into the inter-winding areas between individual wire loops 710A, 710B. The encapsulant 720 can also help adhere winding loops 710A, 710B together, such as to preserve the relative spacing and position of the winding loops 710A, 710B. Preventing moisture ingress and stabilizing the windings can help reduce variation in electrical performance, such as over time or during implant (e.g., the inductance and inter-winding capacitance of the inductive assembly can remain more stable).

To facilitate expansion during implantation, the encapsulant 720 can be selected for elasticity, such as for flexibility, or for bio-compatibility, such as if no bulk encapsulant 730 is used. A material for encapsulant 720 such as medical-grade silicone can provide both elasticity and bio-compatibility.

In certain examples, the bulk encapsulant 730 can serve both to protect the inductive pickup assembly 700 and to secure the inductive wire loops 710A, 710B to mechanical support 705. Examples of bulk encapsulants can include biocompatible overmolding compound, heat-shrink tubing, silicone, or other materials that can be selected for flexibility and bio-compatibility. The outer-most exposed surface of the inductive assembly 700, in the example shown in FIG. 7 the bulk encapsulant 730, can be treated with either a substance that promotes a tissue ingrowth, or an anti-coagulation substance or both, similar to such finish or treatment such as discussed with respect to FIGS. 3A-B, 4A-B. The encapsulant can include a variety of possible over-molding or sheathing materials. The encapsulant need not result in an entirely void-free space. For example, the encapsulant can permit penetration of one or more other elements of the assembly 700. For instance, in some examples, one or more strut structures such as described in previous figures, can penetrate the encapsulant material 730, such as to achieve mechanical or other affixation to the mechanical support 705. In certain examples, such a strut structure can be mechanically or otherwise affixed to the encapsulant material 730. In certain examples, a porous or roughened outer surface can be intentionally developed on the encapsulant material 730, such as to promote tissue ingrowth. In certain examples, only a single insulated wire winding loop 710A is used without any separate support 705.

Figure 8:
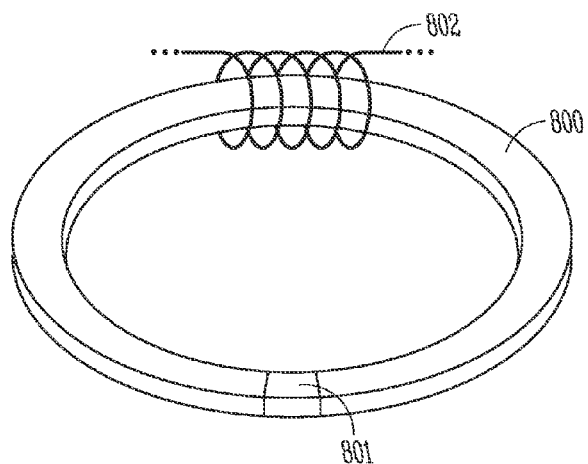
FIG. 8 is a diagram illustrating generally a perspective view of an example of at least a portion of a wireless electrostimulation system including a spiral wire loop wound coaxially to encircle a mechanical support.

FIG. 8 is a diagram illustrating generally a perspective view of an example of at least a portion of a wireless electrostimulation system including a spiral wire loop 802 wound coaxially to encircle a mechanical support 800 or "core." In this example, a non-conductive gap or discontinuity 801 is located along the mechanical support loop 800. The gap 801 can reduce a loss induced by a "shorted secondary effect" of the core 800 when a conductive material is used for the core 800. Such a loss can be due to induced eddy currents in, for example, the mechanical support loop 800. The shorted secondary effect occurs when the core 800 acts like a shorted transformer winding magnetically coupled to the wire loop 802. The electrical effect of such losses can include reduced efficiency or de-tuning of the high-Q inductive antenna/inductive pickup pair in operation. This can be referred to as "antenna pulling." Introducing gap 801 breaks up the induced current loop formed by the core 800 and can reduce loss or antenna pulling effects.

Figure 9:
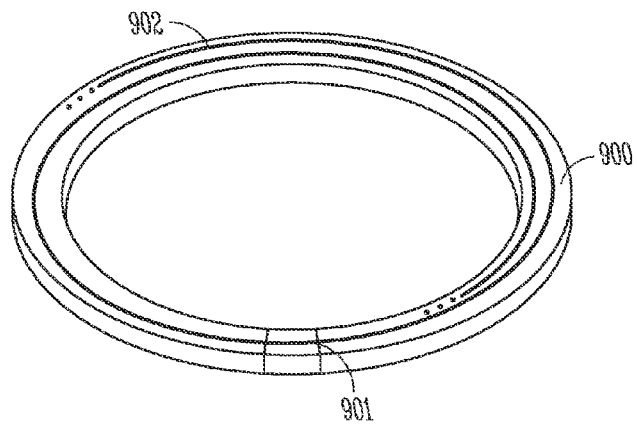
FIG. 9 is a diagram, similar to FIG. 8, but illustrating generally an example of a perspective view of at least a portion of a wireless electrostimulation system including wire loop wound in a spiral on one face of a mechanical support.

FIG. 9 is a diagram, similar to FIG. 8, but illustrating generally a perspective view of an example of at least a portion of a wireless electrostimulation system including wire loop 902 wound in a spiral on a face of a mechanical support 900, and including a non-conductive gap 901, similar to that discussed above with respect to FIG. 8. The examples shown in FIGS. 8-9 demonstrate that different physical arrangements of inductive wire loops 802, 902 can be used, such as with respect to mechanical supports 800, 900. In some examples, FIGS. 8-9 can be combined with the encapsulant or surface treatments discussed in FIG. 7, such as to form a bio-compatible inductive antenna or inductive pickup assembly capable of being implanted within an endocardial location or within the coronary vasculature.

FIG. 10 is a diagram, similar to FIG. 1, but illustrating generally an example of at least a portion of a wireless electrostimulation system 1000 including an external device 1040 configured for generating a time-varying magnetic flux 1014 that can be captured by one or more implantable wireless electrostimulation nodes 1005A, 1005B at a cardiac location 102 inside a patient body 1010. For example, the external device 1040 can be a physician programmer unit comprising a therapy control unit and wireless energy transmission source. In certain examples, the external device 1040 can include a device worn externally by a patient, such as to provide ambulatory electrostimulation therapy on demand or according to a program established by the external device 1040. In certain examples, such as where acute electrostimulation therapy is desired (e.g., in conjunction with percutaneous coronary intervention or other related treatment), the external device 1040 can be incorporated into a bed, vest, hat, chair, or other apparatus that can be worn by or located near the patient, such as for the brief period during which electrostimulus therapy is desired.

Figure 11:
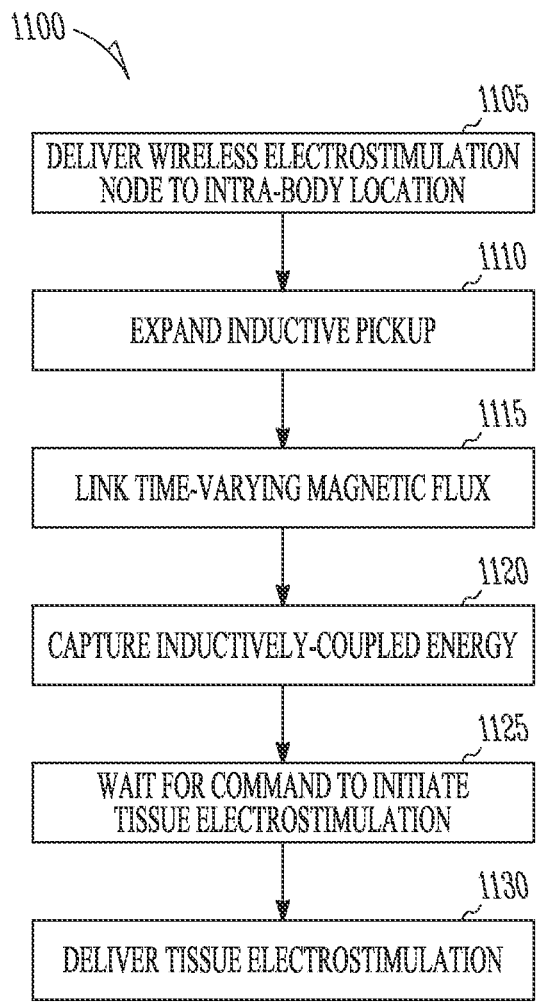
FIG. 11 is a diagram illustrating generally an example of at least a portion of a process including a wireless stimulation node.

FIG. 11 is a diagram illustrating generally an example of at least a portion of a process 1100 that can be performed including a wireless electrostimulation node. In certain examples, the wireless electrostimulation node can be delivered to a location 1105 within a patient's body. An inductive pickup can be expanded at the location 1110, such as using a self-expanding material, or using one or more manipulators, such as passed through a catheter delivery system as shown in FIGS. 5-6. Magnetic flux can be generated by a separate inductive antenna and linked to the inductive pickup 1115. The resulting voltage induced in the inductive pickup results in energy capture 1120. The captured energy can be stored or delivered immediately or upon command. In certain examples, such as shown in FIG. 11, the wireless electrostimulation node can wait for a command to initiate tissue electrostimulation 1125, such as a command from a therapy control unit. Upon receipt of the command, the wireless electrostimulation node then delivers tissue electrostimulation 1130. In some examples, the command and time-varying magnetic flux providing energy for electrostimulation can be the same (e.g., providing nearly instantaneous electrostimulation upon receipt of an appropriate magnetic-flux signal, for instance within a specified range of frequencies, or for a specified duration, such as described above with respect to FIG. 2).

Figure 12:
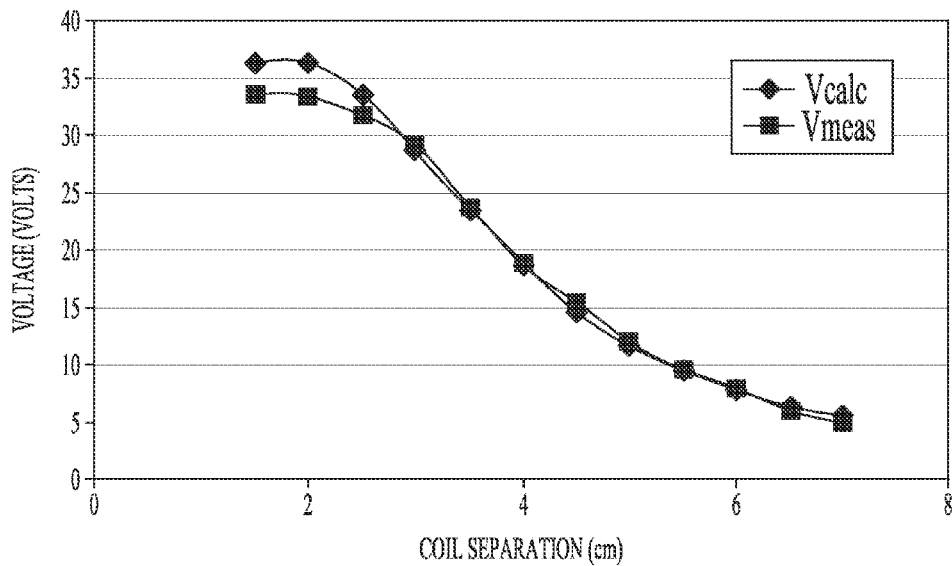
FIG. 12 is an example of a plot showing an analysis of the predicted output voltage developed at an example of a wireless electrostimulation node inductive pickup receiver, and the corresponding actual output voltage when measured on a laboratory model, both plotted versus the separation between an energy transmission source inductive antenna transmitter and wireless electrostimulation node inductive pickup receiver.

FIG. 12 is a plot showing an example of an analysis of an output voltage, ("Vcalc"), predicted at a wireless electrostimulation node inductive pickup receiver. A corresponding actual measured output voltage, ("Vmeas") can be measured across the output electrodes of an inductive pickup receiver of an experimental prototype of the wireless electrostimulation node. The measured output voltage, ("Vmeas"), corresponds to the peak voltage measured on the rising edge of a electrostimulation waveform measured across the wireless electrostimulation node's electrostimulation electrodes, which are coupled to a test load.

Both voltages ("Vcalc," "Vmeas") can be plotted versus the separation (e.g., in centimeters) between (1) an energy transmission source inductive antenna (transmitter) and (2) a wireless electrostimulation node inductive pickup (receiver).

The materials and electrical parameters used for constructing by way of example the experimental prototype described with respect to FIG. 12 are described in TABLE 1. The calculated predicted output voltage shown in FIG. 12, ("Vcalc"), can be estimated by computing $|V_L|$ using EQUATION 2 and the electrical parameters shown in TABLE 1.

TABLE 1

Electrical and Mechanical Parameters Tested for an Example Shown in FIG. 12.

| | |
|---|---|
| Wireless Energy Transmission Source (Transmitter): | 5 cm diameter circular coil made with 10 turns of AWG#25 insulated copper.<br>Total measured series transmitter resistance (coil, FET driver, and capacitor resistances):<br>R = 2.4 Ohms in EQUATION 2.<br>Measured transmitter inductance L = 11.5 µH |

TABLE 1-continued

Electrical and Mechanical Parameters Tested for an Example Shown in FIG. 12.

|  |  |
|---|---|
| | Measured transmitter circuit Q = 30.3<br>Input voltage amplitude $V_0$ = 7.2 Volts (at 1 MHz switched on for 500 uS duration at a repetition rate of 1.2 Hz corresponding to a nominal 72 beat-per-minute pacing rate). |
| Wireless<br>Electrostimulation Node<br>(Receiver): | 1.7 cm diameter circular coil made with 7 turns of 0.005" silver Litz wire. Litz wire comprising 6 parallel strands of insulated 0.002" silver wire<br>Measured receiver resistance r = 0.33 Ohms<br>Measured receiver inductance $L_1$ = 2.0 µH<br>Measured and computed receiver inductance $Q_1$ = 39<br>Tuning capacitor $C_1$ = 0.0116 µF<br>Load: $r_L$ = 500 Ohms for calculation. Actual test load is a 1 kOhm resistor in parallel with a series-combination of a 1 kOhm resistor and 1 uF capacitor. |

Figure 13:
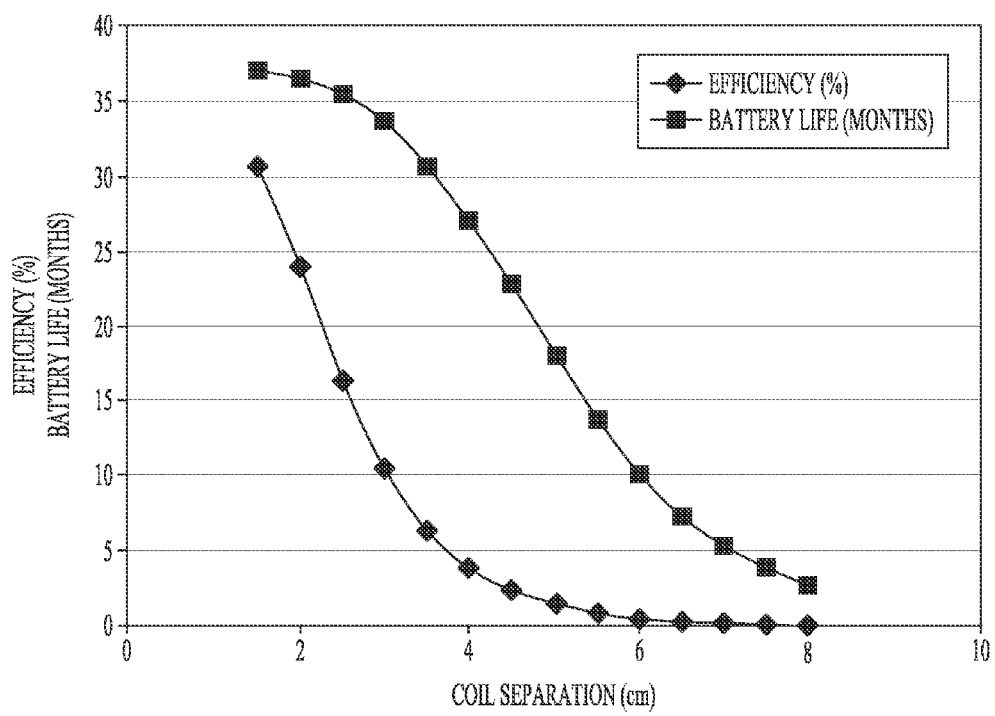
FIG. 13 is an example of a plot from an efficiency analysis showing the computed power coupling efficiency and battery lifetime associated with a given separation between an example of an energy transmission source inductive antenna transmitter and an example of a wireless electrostimulation node inductive pickup receiver.

FIG. 13 is an example of a plot from an efficiency analysis showing the numerically estimated power coupling efficiency, η, in percent (%), and battery lifetime (in months) associated with a given separation between (1) an example of an energy transmission source inductive antenna (transmitter) and (2) an example of a wireless electrostimulation node inductive pickup (receiver)

The power coupling efficiency, η, can be computed from EQUATION 1, such as using the electrical parameters of TABLE 1. Assuming an output voltage of $|V_L|$=3.6 Volts at a coil separation of, for example, 8 cm, as a pacing benchmark, the output power can be computed as $|V_L|^2/(2R_L)$=~0.013 Watts for the duration of the pacing pulse.

The average power output can by computed by multiplying this value by the duty cycle. An example of a cardiac pacing pulse duration is 500 µsec, and an example of a cycle length is 850 msec (corresponding to ~70 heart beats per minute). The resulting duty cycle is 0.00059, and the average output power for a 3.6 volt pacing amplitude is around 7.5 µW.

The input power can be computed by dividing the computed output power, for this example 7.5 µW, by the power coupling efficiency, η, computed from EQUATION 1, and adding the quiescent power consumed by, for example, a microprocessor or microcontroller in the transmitter. Such a quiescent power can be, in an illustrative example, 0.425 µW. Assuming a minimum 3.6 volt pacing amplitude, FIG. 12 shows power coupling efficiencies, η, in percent (%), for a range of separations between the transmitter and receiver coils assuming electrical parameters as are specified in the example in TABLE 1.

Dividing a battery Watt-hour capacity by the output power usage gives an estimate of the battery lifetime. An example of a 25-gram lithium rechargeable battery includes around 12 Watt-hours of useful (recoverable) energy. FIG. 13 shows battery lifetime (in months) for various separations between transmitter and receiver coils assuming electrical parameters as specified in the example in TABLE 1 and assuming, in an illustrative example, a 12 Watt-hr charge available to an implantable transmitter battery.

In the example shown in FIG. 13, battery lifetimes of around three months or longer can be feasible for receiver separations of 8 cm or less at pacing output voltages of 3.6 volts or less.

Received power will diminish as the angle between the planes of the transmit and receive coils deviates from zero degrees (reducing the coupling coefficient, κ), resulting in orientation sensitivity. In some examples, multiple transmit coils in multiple planes, and even multiple coils in a single plane, can help reduce such orientation sensitivity. Multiple receiver coils consume little additional energy in the far field of the transmitter, allowing for examples in which multiple receivers can operate near an inductive transmitter.

In certain examples, such as discussed above, a useful range of 8 cm can be suitable for a transmitter inductive antenna that can be placed against the right ventricular (RV) septum with one or more loop receivers that can be located endocardially on the left ventricular (LV) free wall, for example, even for a dilated heart. In some examples, an inductive receiver on the apical LV free wall can be separated by 4-6 cm from a transmitter in the RV or an external transmitter.

Figure 14:
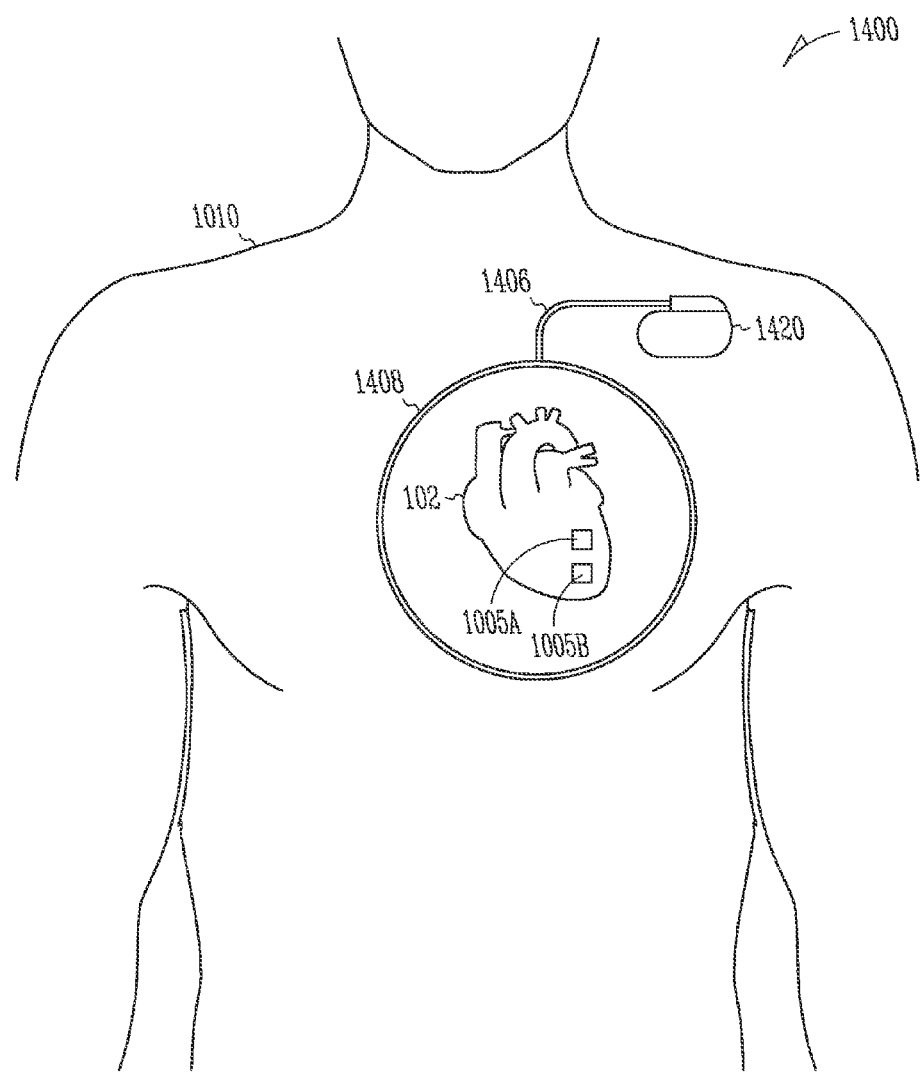
FIG. 14 is a diagram, similar to FIG. 1, but illustrating generally an example of at least a portion of a wireless electrostimulation system including a subcutaneous inductive antenna.

FIG. 14 is a diagram, similar to FIG. 1, but illustrating generally an example of at least a portion of a wireless electrostimulation system 1400 including a subcutaneous inductive antenna. In some examples, an implantable transmitter inductive antenna 1408 need not be located endocardially within a heart 102, and may be placed subcutaneously on the chest of a patient 1010, or in the pericardial space adjacent to the heart 102.

An inductive antenna feedwire assembly 1406 can be electrically coupled between (1) an inductive antenna 1408 at a distal end of the feedwire assembly 1406, and (2) an implantable cardiac rhythm management device 1420 at a proximal end of the feedwire assembly 1406. In some examples, an inductive antenna 1408 generates a time-varying magnetic flux to be captured by electrostimulation electrode assemblies 1005A, 1005B.

In some examples, the inductive antenna 1408 and feedwire assembly 1406 can be constructed similarly to, for example, an endocardial flexible lead system (e.g., a biocompatible silicone outer jacket can be selected for an outer surface of the feedwire assembly 1406, and one or more coiled metallic conductors insulated from one another can be used internally to the assembly 1406 to energize an inductive antenna 1408).

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "a" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A wireless electrostimulation device, comprising:
    an implantable seed having a proximal end, a distal end, and a longitudinal axis extending from the proximal end to the distal end;
    the implantable seed including a proximal portion having a distally extending opening defined at least in part by a side wall;
    a tissue attachment mechanism positioned proximate the distal end of the implantable seed, the tissue attachment mechanism configured to secure the implantable seed to cardiac tissue;
    a first electrostimulation electrode configured to contact cardiac tissue when the implantable seed is secured to cardiac tissue;
    a second electrostimulation electrode;
    wherein the first and second electrostimulation electrodes form an electrostimulation circuit to provide an electrical stimulus to cardiac tissue; and
    a retention pin located proximate the proximal end of the implantable seed, the retention pin extending across the opening in the proximal portion of the implantable seed and secured to the side wall on opposing sides of the opening.

2. The wireless electrostimulation device of claim 1, wherein the proximal portion of the implantable seed has an annular shape defining the opening, and
    the retention pin is secured to the annular proximal portion with the retention pin extending across the opening.

3. The wireless electrostimulation device of claim 2, wherein a space is defined between an interior surface of the annular proximal portion and the retention pin.

4. The wireless electrostimulation device of claim 2, wherein the annular proximal portion of the implantable seed extends proximal of the retention pin.

5. The wireless electrostimulation device of claim 1, wherein an outer surface of the proximal portion of the implantable seed is cylindrical.

6. The wireless electrostimulation device of claim 5, wherein the retention pin is cylindrical.

7. The wireless electrostimulation device of claim 1, wherein the retention pin is configured to be engaged by a component of an intravascular delivery system during implantation of the implantable seed.

8. The wireless electrostimulation device of claim 1, wherein the retention pin is cylindrical.

9. A wireless electrostimulation system, comprising:
    an implantable seed including:
        a housing having a proximal end, a distal end, and a longitudinal axis extending from the proximal end to the distal end;
        a tissue attachment mechanism positioned proximate the distal end of the housing, the tissue attachment mechanism configured to secure the implantable seed to cardiac tissue;
        a retention pin located proximate the proximal end of the housing, with the retention pin extending between a first side and an opposing second side of an opening defined by the proximal end of the housing; and
    an intravascular delivery system including:
        a delivery catheter having a distal end region surrounding the implantable seed during delivery of the implantable seed to cardiac tissue; and
        a retention feature configured to engage the retention pin while the implantable seed is positioned in the distal end region of the delivery catheter.

10. The wireless electrostimulation system of claim 9, wherein the retention feature surrounds the retention pin.

11. The wireless electrostimulation system of claim 10, wherein the retention feature is releasable from the retention pin upon implantation of the implantable seed into cardiac tissue.

12. The wireless electrostimulation system of claim 9, wherein the retention feature includes a flexible member extending proximally from the retention pin.

13. The wireless electrostimulation system of claim 12, wherein proximal movement of the flexible member away from the retention pin releases the flexible member from the retention pin.

14. The wireless electrostimulation system of claim 9, wherein the retention pin is oriented perpendicular to the longitudinal axis of the housing.

15. The wireless electrostimulation system of claim 10, wherein the retention pin is cylindrical.

16. The wireless electrostimulation system of claim 15, wherein the proximal portion of the implantable seed extends proximal of the retention pin.

17. The wireless electrostimulation system of claim 16, wherein an outer surface of the proximal portion of the housing is cylindrical.

* * * * *